United States Patent
Asada et al.

(10) Patent No.: US 11,854,331 B2
(45) Date of Patent: Dec. 26, 2023

(54) BANKNOTE MANAGEMENT METHOD AND BANKNOTE MANAGEMENT SYSTEM

(71) Applicant: Glory Ltd., Hyogo (JP)

(72) Inventors: Toshihide Asada, Hyogo (JP); Yasuhiro Matsumoto, Hyogo (JP)

(73) Assignee: GLORY LTD., Hyogo (JP)

( * ) Notice: Subject to any disclaimer, the term of this patent is extended or adjusted under 35 U.S.C. 154(b) by 85 days.

(21) Appl. No.: 17/570,389

(22) Filed: Jan. 7, 2022

(65) Prior Publication Data

US 2022/0237980 A1    Jul. 28, 2022

(30) Foreign Application Priority Data

Jan. 28, 2021   (JP) ................................. 2021-012378

(51) Int. Cl.
  *G07D 11/32*    (2019.01)
  *A61L 2/10*    (2006.01)

(52) U.S. Cl.
  CPC ............... *G07D 11/32* (2019.01); *A61L 2/10* (2013.01)

(58) Field of Classification Search
  None
  See application file for complete search history.

(56) References Cited

U.S. PATENT DOCUMENTS 9,594,954 B1 *   3/2017  Walker ................ G06V 30/416

FOREIGN PATENT DOCUMENTS

| EP | 1 531 432 A2 | 5/2005 |
| JP | 2015-56010 A | 3/2015 |

OTHER PUBLICATIONS

Extended European Search Report dated Jun. 23, 2022, in corresponding European Application No. 22151033.2.

* cited by examiner

*Primary Examiner* — Kristy A Haupt
(74) *Attorney, Agent, or Firm* — XSENSUS LLP

(57) ABSTRACT

A banknote management system includes a first banknote processing apparatus including a first serial number reading apparatus configured to read a serial number of a banknote, and a first disinfection apparatus configured to disinfect the banknote; a recording apparatus; and processing circuitry configured to receive the serial number of the banknote read by the first serial number reading apparatus and first disinfection information, and record the serial number and the first disinfection information in association with each other in the recording apparatus, the first disinfection information being information relating to a state of disinfection of the banknote disinfected by the first disinfection apparatus.

20 Claims, 13 Drawing Sheets

BANKNOTE MANAGEMENT METHOD AND BANKNOTE MANAGEMENT SYSTEM

CROSS-REFERENCE TO RELATED APPLICATION

This application is entitled to (or claims) the benefit of Japanese Patent Application No. 2021-012378, filed on Jan. 28, 2021, the disclosure of which including the specification, drawings and abstract is incorporated herein by reference in its entirety.

TECHNICAL FIELD

The present disclosure relates to a banknote management method and a banknote management system.

BACKGROUND

Conventionally, various banknote management methods and banknote management systems are known as disclosed in PTL 1, for example.

In recent years, there has been a growing interest in the cleanliness of banknotes, especially with regard to the adhesion of bacteria and viruses to banknotes.

CITATION LIST

Patent Literature

PTL 1
Japanese Patent Application Laid-Open No. 2015-056010

SUMMARY

The banknote management method according to the present disclosure is a banknote management method performed by a computer, and includes receiving the serial number of the banknote and first disinfection information that is information relating to the state of the disinfection of the banknote, and recording the serial number and the first disinfection information in association with each other in a recording apparatus. In the present disclosure, the term computer is a concept that encompasses not only electronic calculators with processors or CPUs (Central Processing Units), but also the processor itself and the CPU itself.

DETAILED DESCRIPTION

Figure 1A:
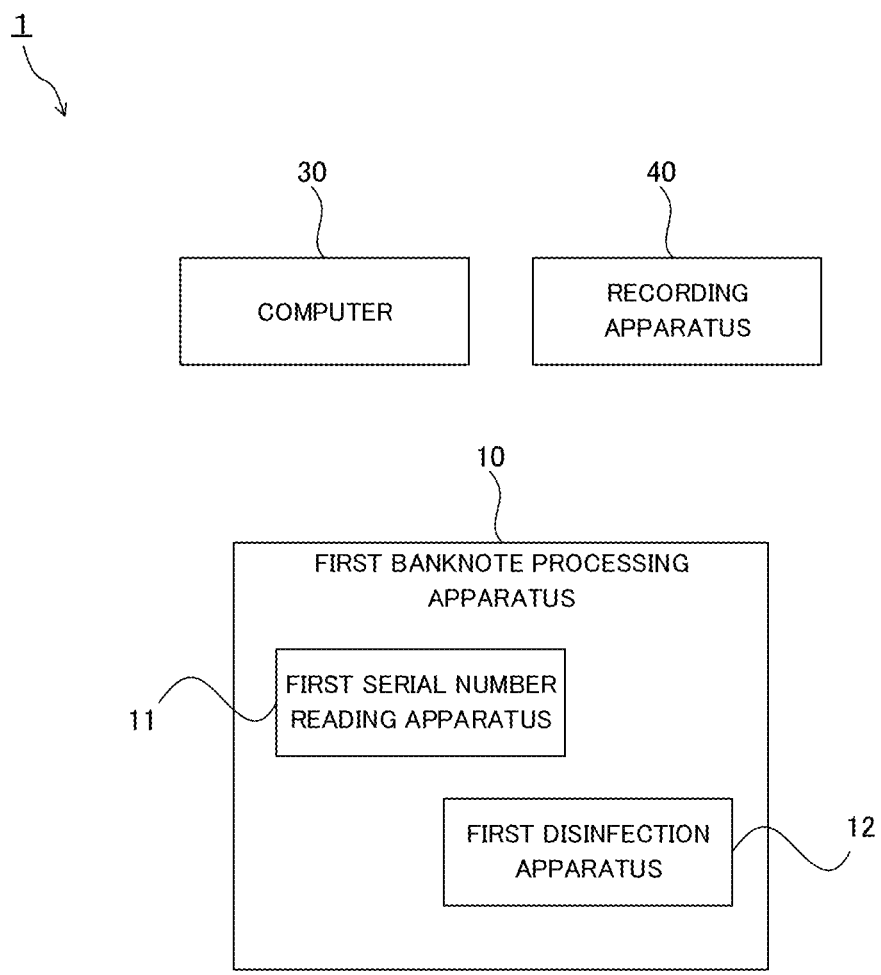
FIG. 1A is a schematic view of a banknote management system according to Embodiment 1.

Disinfection of banknotes can eliminate or reduce the effects of bacteria and viruses, but no known banknote management method or system can control the state of disinfection of banknotes, such as whether or not each banknote has been disinfected, or to what extent it has been disinfected. If the status of disinfection of banknotes is not known, smooth processing of banknotes may not be possible.

An object of the present disclosure is to provide a banknote management method and a banknote management system that support the smooth processing of banknotes.

In addition, in the banknote management method according to the present disclosure, the first disinfection information may be information representing whether the banknote has been disinfected.

In addition, in the banknote management method according to the present disclosure, the first disinfection information may be information representing the degree of the disinfection of the banknote. In addition, the first disinfection information may be an index associated with the residual quantity or activity of the bacteria or virus adhering on the banknote.

In addition, in the banknote management method according to the present disclosure, the banknote may include a first banknote, and a second banknote that is stored in a stacked state on the first banknote, the banknote management method may further include receiving a serial number of the first banknote, receiving first disinfection information of the first banknote that is information relating to a state of disinfection of the first banknote, receiving a serial number of the second banknote, and receiving first disinfection information of the second banknote that is information relating to a state of disinfection of the second banknote, and updating the first disinfection information of the first banknote in accordance with the first disinfection information of the second banknote when the first disinfection information of the second banknote indicates that the first disinfection information of the second banknote is inferior to the first disinfection information of the first banknote in terms of a state of disinfection.

In addition, in the banknote management method according to the present disclosure, the updating of the first disinfection information of the first banknote in accordance with the first disinfection information of the second banknote may be replacement of the first disinfection information of the first banknote with the first disinfection information of the second banknote.

In addition, in the banknote management method according to the present disclosure, the computer may be communicatively connected to a first banknote processing apparatus, the first banknote processing apparatus including a first serial number reading apparatus and a first disinfection apparatus, the serial number may be a serial number of the banknote read by the first serial number reading apparatus, and the first disinfection information may be information relating to a state of disinfection of the banknote performed by the first disinfection apparatus. In addition, the computer may be separated from the first banknote processing apparatus. In addition, the computer may be incorporated in the first banknote processing apparatus (that is, the control apparatus (CPU) of the first banknote processing apparatus may function as the computer).

In addition, in the banknote management method according to the present disclosure, the computer may be communicatively connected to a second banknote processing apparatus, the second banknote processing apparatus including a second serial number reading apparatus, and the banknote management method may further include receiving a serial number of the banknote read by the second serial number reading apparatus; and determining details of a process to be performed on the banknote by the second banknote processing apparatus in accordance with the first disinfection information. In addition, the computer may be incorporated in the second banknote processing apparatus (that is, the control apparatus (CPU) of the second banknote processing apparatus may function as the computer).

In addition, in the banknote management method according to the present disclosure, the determining of the details of the process to be performed on the banknote by the second banknote processing apparatus may include determining whether disinfection is to be performed on the banknote by a second disinfection apparatus provided in the second banknote processing apparatus.

In addition, the banknote management method according to the present disclosure may further include receiving second disinfection information that is information relating to a state of disinfection of the banknote performed by the second disinfection apparatus provided in the second banknote processing apparatus, and updating the first disinfection information recorded in the recording apparatus in accordance with the second disinfection information when, after the serial number is read by the first serial number reading apparatus and the banknote is disinfected by the first disinfection apparatus, the serial number is read by the second serial number reading apparatus, and the banknote is disinfected by the second disinfection apparatus.

In addition, in the banknote management method according to the present disclosure, the recording apparatus may be installed in a container in which the banknote is stored when the banknote is transported. The container may be cassettes, pouches (bags for sealing), bags, etc.

In addition, in the banknote management method according to the present disclosure, the disinfection may be performed through at least one of irradiation of the banknote with an ultraviolet ray, contact between the banknote and a disinfecting material, and heating of the banknote. The ultraviolet ray need only be light with a wavelength $\lambda$ of 10 nm$\leq\lambda\leq$400 nm, and for example, light of 260 nm may be used as an ultraviolet ray. The disinfecting material may be any of gas, liquid and solid.

In addition, the banknote management method according to the present disclosure may further include determining an index representing the ease of handling of the banknote in accordance with the first disinfection information; and outputting the index. The outputting may be indication on a screen of the computer or the banknote processing apparatus storing the banknote, printing to paper, or transmission of information to the computer used by one (e.g., security transport institution) that handles the banknote.

In addition, a banknote management system according to the present disclosure includes a first banknote processing apparatus including a first serial number reading apparatus configured to read a serial number of a banknote, and a first disinfection apparatus configured to disinfect the banknote, a recording apparatus, a computer configured to receive the serial number of the banknote read by the first serial number reading apparatus and first disinfection information, and record the serial number and the first disinfection information in association with each other in the recording apparatus, the first disinfection information being information relating to a state of disinfection of the banknote disinfected by the first disinfection apparatus. In addition, the computer may be separated from the first banknote processing apparatus. In addition, the computer may be incorporated in the first banknote processing apparatus (that is, the control apparatus (CPU) of the first banknote processing apparatus may function as the computer).

In addition, the banknote management system according to the present disclosure may further include the second banknote processing apparatus including a second serial number reading apparatus configured to read the serial number of the banknote. The computer may be configured to determine details of a process to be performed on the banknote by the second banknote processing apparatus in accordance with the first disinfection information. In addition, the computer may be separated from the second banknote processing apparatus. In addition, the computer may be incorporated in the second banknote processing apparatus (that is, the control apparatus (CPU) of the second banknote processing apparatus may function as the computer).

In addition, in the banknote management system according to the present disclosure, the second banknote processing apparatus may include a second disinfection apparatus configured to disinfect the banknote, and the computer may be configured to update the first disinfection information recorded in the recording apparatus in accordance with second disinfection information when, after the serial number of the banknote is read by the first serial number reading apparatus and the banknote is disinfected by the first disinfection apparatus, the serial number of the banknote is read by the second serial number reading apparatus, and the banknote is disinfected by the second disinfection apparatus.

In addition, in the banknote management system according to the present disclosure, the first banknote processing apparatus and the second banknote processing apparatus may be disposed in a same facility. In this case, the transport of banknotes between these apparatuses may be performed through a container, or through a transport apparatus or a transport robot that does not require manual operations.

In addition, in the banknote management system according to the present disclosure, the first banknote processing apparatus and the second banknote processing apparatus may be disposed in facilities different from each other.

In addition, the banknote management system according to the present disclosure may further include a container configured to be detachable to the first banknote processing apparatus and the second banknote processing apparatus, and to store the banknote in an externally inaccessible manner.

In addition, the banknote management method according to the present disclosure may further include erasing the first disinfection information recorded associated with the serial number in the recording apparatus or updating the first disinfection information recorded associated with the serial number in the recording apparatus to information indicating that disinfection has not been made when the banknote is ejected from the first banknote processing apparatus or the second banknote processing apparatus in the state where it can be directly touched by the user of the first banknote processing apparatus or the second banknote processing apparatus.

In addition, in the banknote management method according to the present disclosure, the index indicating the ease of handling of the banknote may be a fee for handling the banknote, the type (category or level) of the material that should be put on or the tool that should be used for handling the banknote.

In addition, in the banknote management method according to the present disclosure, the first disinfection information may be an index associated with the residual quantity or activity of the bacteria or virus adhering on the banknote.

In addition, in the banknote management method according to the present disclosure, the first disinfection information may be automatically updated in accordance with the time length for which the banknote remains in the first banknote processing apparatus. In other words, the computer may change the first disinfection information so as to indicate that the state of the disinfection is superior over time. For example, in the case where the target virus is known to be inactivated over time, the first disinfection information may be changed to information indicating that the state of the disinfection is superior over time after the disinfection. In addition, in the case where the banknote is ejected from the first banknote processing apparatus or the second banknote processing apparatus in the state where it can be directly touched by the worker or the user, the first banknote processing apparatus or the second banknote processing apparatus may send a predetermined signal to the computer. The predetermined signal is a signal that indicates ejection of a banknote in a state where it can be directly touched and the serial number of this banknote. When receiving this signal, the computer may send, to the recording apparatus, a command to erase the first disinfection information recorded in association with the serial number of the banknote, or update it to information indicating that disinfection has not been made.

The present disclosure can provide a banknote management method and a banknote management system that support the smooth processing of banknotes.

The following is a detailed description of an embodiment of the present disclosure with reference to the drawings. Although this specification describes configurations or concepts with counter suffix such as "first" and "second", such as "the first banknote processing apparatus 10", these suffixes are merely a convenience to help distinguish multiple identical or similar configurations or concepts from each other. Therefore, in some cases, the configuration or concept with the suffix "first" and the configuration or concept with the suffix "second" are replaceable with each other.

Embodiment 1

FIG. 1A is a schematic view of a banknote management system 1 according to Embodiment 1. The banknote management system 1 includes a first banknote processing apparatus 10, a computer 30 and a recording apparatus 40.

The first banknote processing apparatus 10 is an apparatus for processing banknotes that is installed in a financial institution such as a bank, a distribution store such as convenience store or a facility such as a security transport institution. Specific examples of it include a banknote coin depositing machine, a banknote coin depositing and dispensing machine, an automatic teller machine, a tax payment machine, a money changer, a teller machine, a ticket vending machine, a vending machine, a change machine, a sales depositing and dispensing machine, a banknote counter, a banknote sorting machine, a banknote recycler, a banknote bundler, an electronic money charging machine, and a banknote disinfection apparatus.

The first banknote processing apparatus 10 includes a first serial number reading apparatus 11 and a first disinfection apparatus 12.

The first serial number reading apparatus 11 reads the serial number from the banknote processed by the first banknote processing apparatus 10. The first serial number reading apparatus 11 may be a recognition unit that reads serial numbers and recognizes the denomination, fitness, authentication and the like of banknotes.

The first disinfection apparatus 12 disinfects the banknote processed by the first banknote processing apparatus 10. Note that the disinfection of the banknote itself may be the processing of banknotes performed by the first banknote processing apparatus 10. The first disinfection apparatus 12 may include one or more of an ultraviolet ray irradiation apparatus, a disinfection material supply apparatus and a heating apparatus.

In the case where the first disinfection apparatus 12 includes an ultraviolet ray irradiation apparatus, the disinfection is performed through irradiation of an ultraviolet ray on banknotes. In the case where the first disinfection apparatus 12 includes a disinfection material supply apparatus, the disinfection is performed through a contact between the banknote and the disinfecting material. Note that the disinfecting material may be liquid, gas, or powder. In addition, in the case where the first disinfection apparatus 12 includes a heating apparatus, the disinfection is performed through heating of banknotes.

Note that the disinfection as used herein is the removal or reduction of the infectivity of bacteria or viruses that may cause disease in humans or other organisms, and is a concept that encompasses sterilization, making inactive condition, inactivation, or destruction.

The computer 30 is hardware including a computation apparatus such as a CPU, a recording apparatus that records data such as a program, and an interface that transmits and receives information to/from the outside of the computer 30 and the like. The computer 30 is configured to perform various operations when the computation apparatus executes a program recorded in the recording apparatus 40. The computer 30 is a server apparatus communicatively connected to the first banknote processing apparatus 10 through a network such as the Internet, for example. In an exemplary implementation, the computer 30 is encompassed by or may include processing circuitry which will be discussed later with respect to FIG. 11.

The recording apparatus 40 is a recording apparatus communicatively connected to the computer 30 through a network such as the Internet, for example. Specific examples of the recording apparatus 40 include a semiconductor memory such as a read only memory (ROM), a random access memory (RAM), and a solid state drive (SSD), and a recording medium such as a hard disk drive (HDD). In an exemplary implementation, the recording apparatus 40 is encompassed by or may include a memory which will be discussed later with respect to FIG. 11.

Figure 1B:
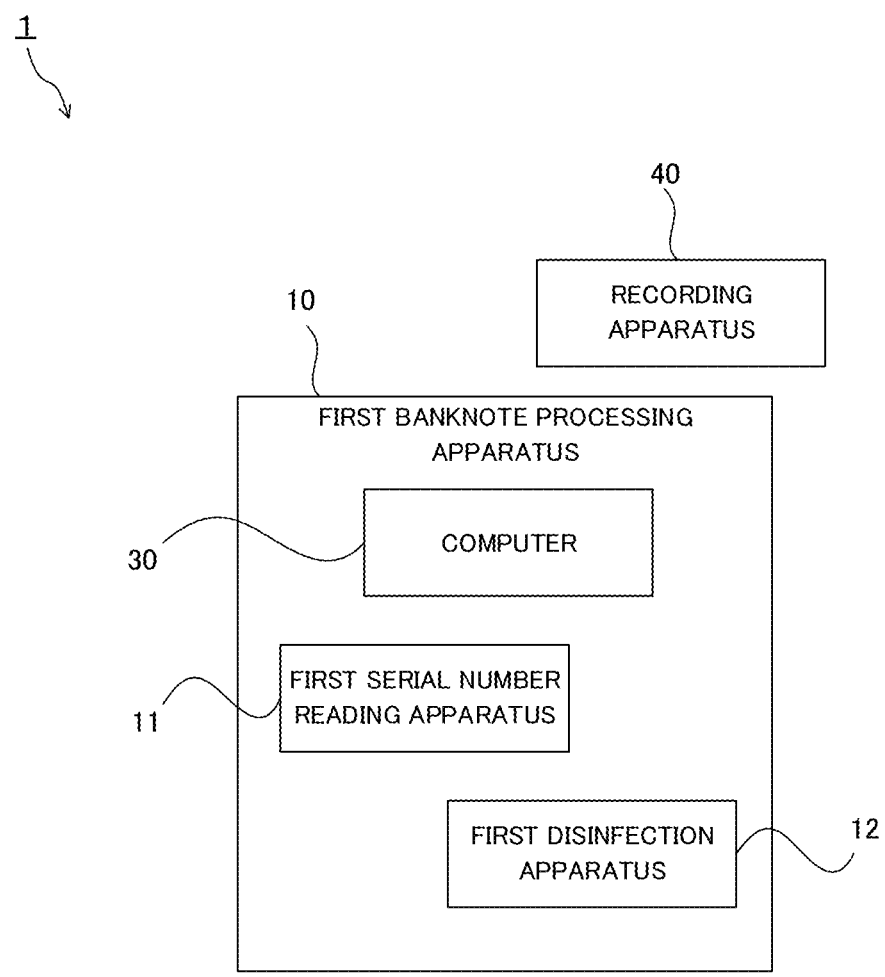
FIG. 1B is a schematic view of a banknote management system according to a modification of Embodiment 1.
Figure 1C:
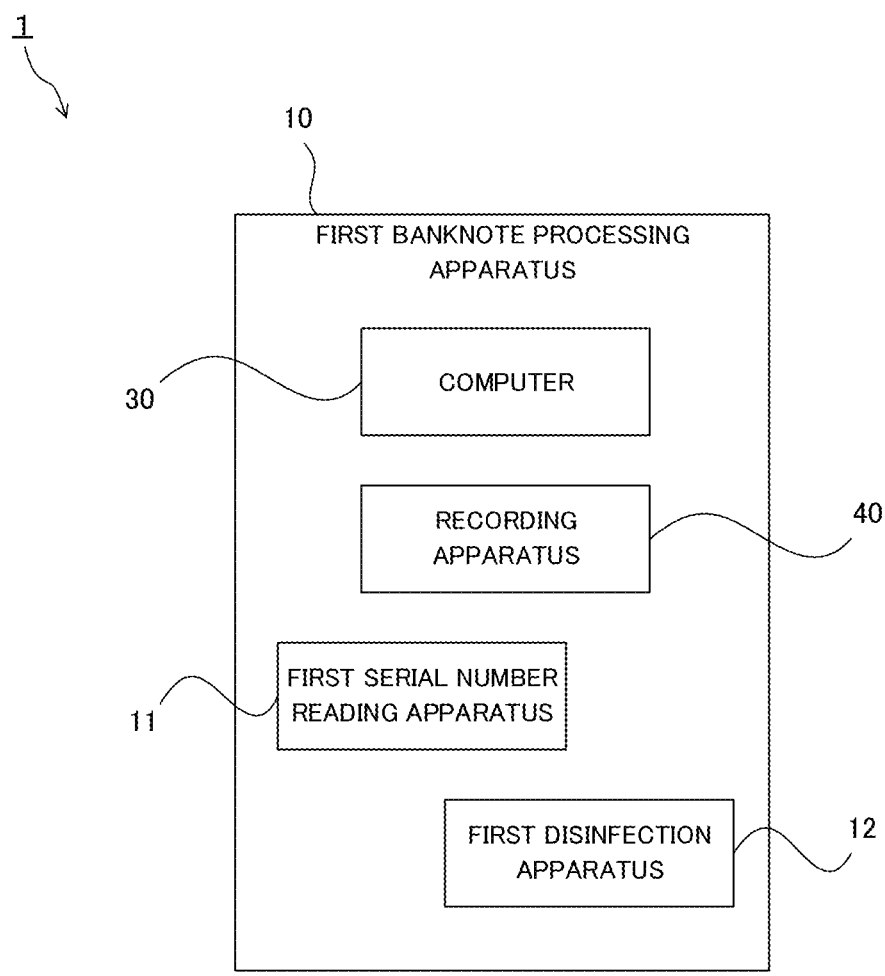
FIG. 1C is a schematic view of a banknote management system according to another modification of Embodiment 1.

FIG. 1B and FIG. 1C are schematic views of the banknote management system 1 according to a modification of Embodiment 1. As in the modification illustrated in FIG. 1B, the computer 30 may be provided in the first banknote processing apparatus 10, and may be a control apparatus (processor or CPU) of the first banknote processing apparatus 10 that entirely controls the first banknote processing apparatus 10. In addition, as in the modification illustrated in FIG. 1C, the recording apparatus 40 may be provided in the first banknote processing apparatus 10, and may be a recording apparatus that records programs to be executed by the computer 30 (the control apparatus of the first banknote processing apparatus 10) to control the first banknote processing apparatus 10. By comparison with Embodiment 1 illustrated in FIG. 1A, the modification illustrated in FIG. 1B differs only in whether the computer 30 is a separate computer separated from the first banknote processing apparatus 10, or is a control apparatus provided in the first banknote processing apparatus 10. In addition, by comparison with the modification illustrated in FIG. 1B, the modification illustrated in FIG. 1C differs only in whether the recording apparatus 40 is a separate recording apparatus separated from the first banknote processing apparatus 10, or is a recording apparatus provided in the first banknote processing apparatus 10. Note that the recording apparatus 40 may be a recording apparatus provided in the computer 30 (see FIG. 1A) as a separate member separated from the first banknote processing apparatus 10.

The description is continued below with reference to FIG. 1A. In the banknote management system 1 with the above-described configuration, banknotes are managed in the following manner.

Figure 2:
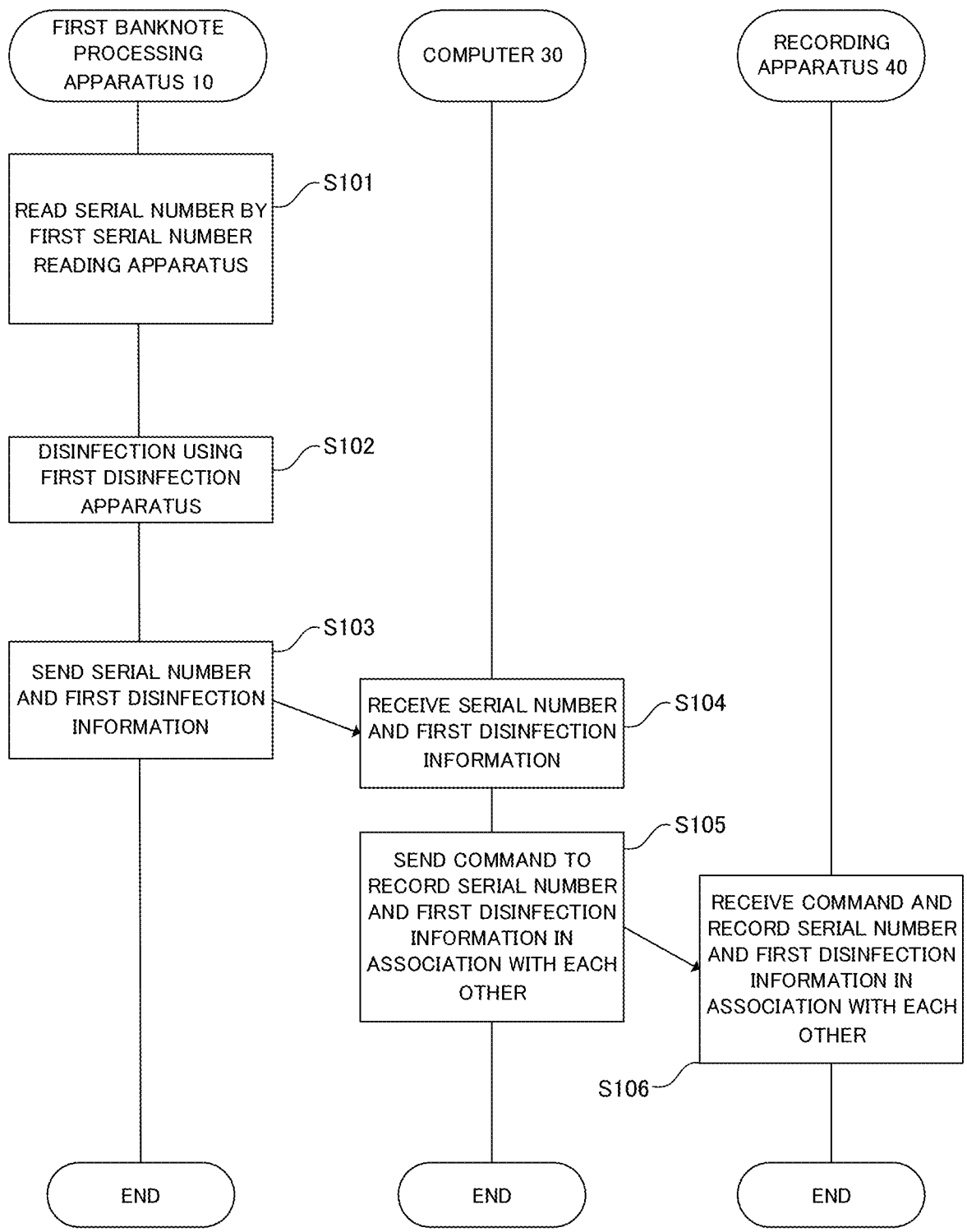
FIG. 2 is a sequence diagram illustrating a banknote management method in the banknote management system according to Embodiment 1.

FIG. 2 is a sequence diagram illustrating a banknote management method in the banknote management system 1.

First, when receiving a banknote to be processed, the first banknote processing apparatus 10 reads the serial number from the banknote by the first serial number reading apparatus 11 (S101). Subsequently, with the first disinfection apparatus 12, the first banknote processing apparatus 10 disinfects the banknote whose serial number has been read (S102). Thereafter, the first banknote processing apparatus 10 sends, to the computer 30, the serial number of this banknote and first disinfection information of this banknote (S103). At this time, the first banknote processing apparatus 10 sends, to the computer 30, the serial number and the first disinfection information in the state where they are associated with each other. The computer 30 receives the serial number sent from the first banknote processing apparatus 10 (which may be construed as the first serial number reading apparatus 11 and the first disinfection apparatus 12) (S104).

The first disinfection information is information relating to the state of the disinfection of the banknote, such as information representing whether the banknote has been disinfected. In addition, the first disinfection information may be information representing the degree of the disinfection of the banknote, for example. The degree of the disinfection of the banknote may be a level represented by a numerical value or the like that is determined based on the specific aspect of the disinfection. For example, the degree of the disinfection may be represented by a numerical value that increases (or decreases) when the disinfection is performed by a method with a high disinfection effect. The degree of the disinfection may be determined based on whether the disinfection has been performed by irradiation of an ultraviolet ray, a contact with the disinfecting material, or heating. In the case where it is performed through irradiation of an ultraviolet ray, the degree of the disinfection may be determined based on the reliability of the disinfection through the irradiation of an ultraviolet ray such as the intensity, wavelength or irradiation time of the ultraviolet ray. In the case where it is performed through the contact with the disinfecting material, the degree of the disinfection may be determined based on the reliability of the disinfection through the contact with the disinfecting material such as the density or type of the material. In the case where it is performed through heating, the degree of the disinfection may be determined based on the reliability of the disinfection through the heating such as the heating temperature or heating time. As a simple example, it is possible to determine the degree of the disinfection such that the longer the irradiation time, the greater the state of the disinfection, and that the shorter the irradiation time, the lower the state of the disinfection, even with the same intensity and wavelength of the ultraviolet ray. The relationship between the condition of the disinfection and the reduction of the infectivity of the bacteria or virus adhering on the banknote may be experimentally determined in advance so as to determine the degree of the disinfection based on the experiment result.

Note that the first banknote processing apparatus 10 may perform the reading of the serial number prior to the disinfection of the banknote, or may perform the disinfection of the banknote prior to the reading of the serial number. In addition, to the computer 30, the first banknote processing apparatus 10 may send the serial number and the first disinfection information at the same time, send the serial number prior to the first disinfection information, or send the first disinfection information prior to the serial number. For example, S103 may branch to the step of sending the serial number and the step of sending the first disinfection information, the step of sending the serial number may be performed between S101 and S102, and the step of sending the first disinfection information may be performed after S102. In this case, naturally, S104 also branches to two steps. Note that when the serial number and the first disinfection information are transmitted and received at different timings, the first banknote processing apparatus 10 may operate in the following manner such that the computer 30 can associate the serial number and the first disinfection information with each other. Specifically, the first banknote processing apparatus 10 may send the serial number and the first disinfection information to the computer 30, with some key information (e.g., the processing time or processing order of banknotes) added to at least one of the serial number and the first disinfection information.

When receiving the serial number and the first disinfection information (S104), the computer 30 sends, to the recording apparatus 40, a command to record the serial number and the first disinfection information in association with each other (S105). Naturally, information representing the serial number and the first disinfection information is included in this command.

When receiving the command from the computer 30, the recording apparatus 40 records the serial number and the first disinfection information in association with each other in accordance with the command (S106).

The above-described banknote management method can manage the state of the disinfection of each banknote processed by the first banknote processing apparatus 10 in association with the serial number. Thus, how or how carefully each banknote should be handled after the processing at the first banknote processing apparatus 10 can be appropriately determined. Thus, the subsequent banknote processing can be smoothly performed.

In the banknote management system according to Embodiment 1, the following banknote management method may also be performed. In this case, the first banknote processing apparatus 10 processes a first banknote and a second banknote as the banknote. In addition, the first banknote processing apparatus 10 includes a storage unit. This storage unit stores a plurality of banknotes in a stacked state. Specifically, the first banknote is stored in the storage unit, and the second banknote is stored in the storage unit in a state where it is stacked on the first banknote. Examples of the storage unit include a cassette, a stacking unit (receptacle) with an opening, and the like.

Figure 3:
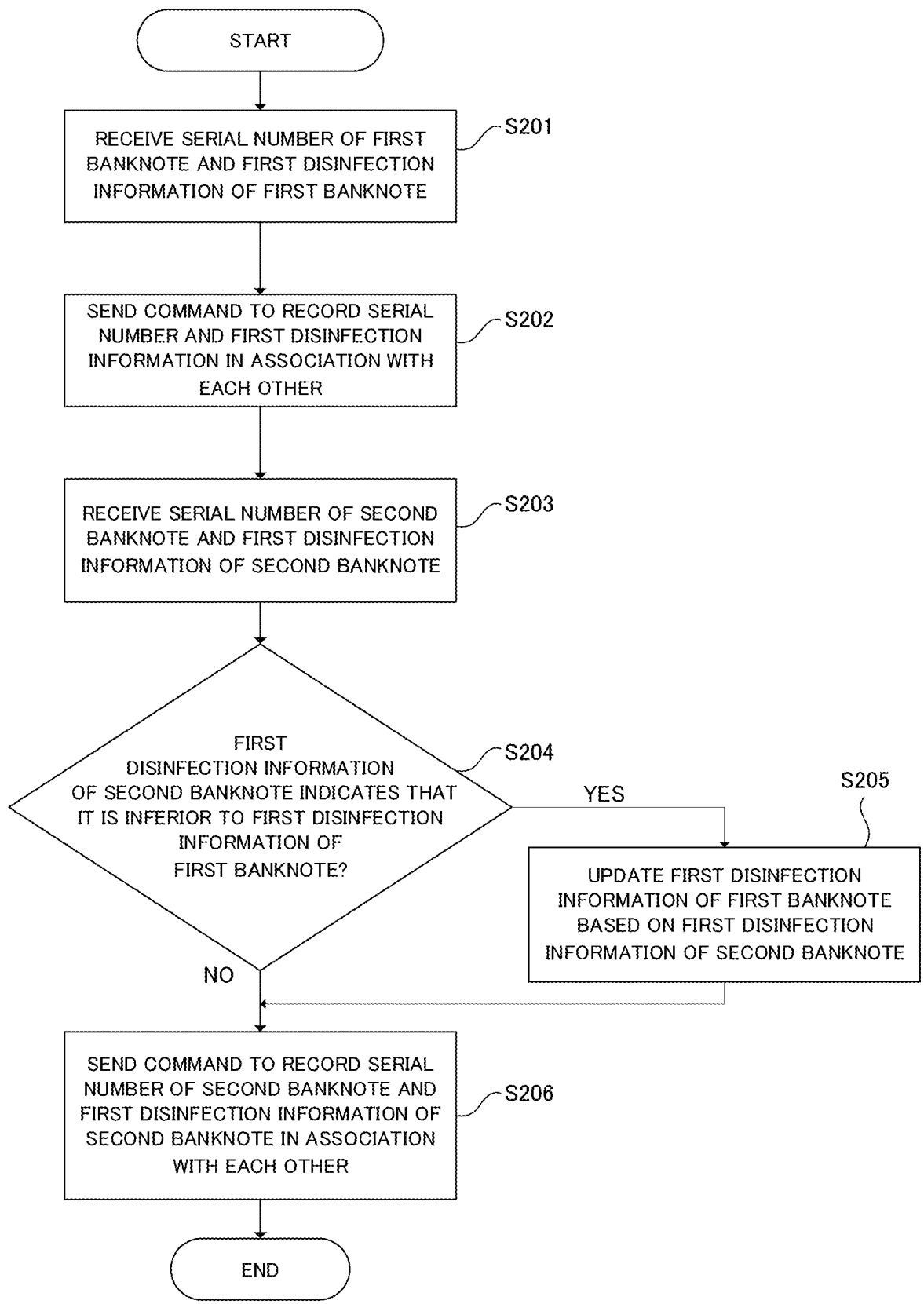
FIG. 3 is a flowchart illustrating a banknote management method in the banknote management system according to Embodiment 1.

FIG. 3 is a flowchart illustrating a banknote management method in the banknote management system 1, and in particular, a step performed by the computer 30. The matters overlapping the description of FIG. 2 may be omitted.

First, the computer 30 receives the serial number of the first banknote and the first disinfection information of the first banknote sent from the first banknote processing apparatus 10 (S201). S201 and S202 may be performed at different timings.

When receiving the serial number of the first banknote and the first disinfection information of the first banknote, the computer 30 sends, to the recording apparatus 40, a command to record the serial number of the first banknote and the first disinfection information of the first banknote in association with each other (S202).

Subsequently, the computer 30 receives the serial number of the second banknote and the first disinfection information of the second banknote sent from the first banknote processing apparatus 10 (S203).

Next, after making an inquiry of the recording apparatus 40 about the first disinfection information of the first banknote as necessary, the computer 30 determines whether the first disinfection information of the second banknote indicates that it is inferior to the first disinfection information of the first banknote in terms of the state of the disinfection (S204).

In the case where the first disinfection information of the second banknote indicates that it is inferior to the first disinfection information of the first banknote in terms of the state of the disinfection (S204: YES), the computer 30 updates the first disinfection information of the first banknote on the basis of the first disinfection information of the second banknote (S205). To be more specific, it sends a command, to the recording apparatus 40, to generate new first disinfection information and record this new first disinfection information in association with the serial number of the first banknote. The recording apparatus 40 receiving this command updates the first disinfection information of the first banknote recorded in association with the serial number of the first banknote, to new first disinfection information. The new first disinfection information may be the first disinfection information of the second banknote itself. In this case, the update of the first disinfection information of the first banknote is replacement with the first disinfection information of the second banknote. The new first disinfection information may be information representing the degree of the disinfection between the degree of the disinfection of the first banknote and the degree of the disinfection of the second banknote.

In the case where the first disinfection information of the second banknote does not indicate that it is inferior to the first disinfection information of the first banknote in terms of the state of the disinfection (S204: NO), and the case where the first disinfection information of the first banknote is updated (after S205), the computer 30 sends, to the recording apparatus 40, a command to record the serial number of the second banknote and the first disinfection information of the second banknote in association with each other (S206).

Note that the step indicated in S206 may be performed between the step indicated in S203 and the step indicated in S204.

With the management method described above, in the case where a banknote with the inferior state of the disinfection is stored in the storage unit later, the first disinfection information of the banknote with the superior state of the disinfection can be updated based on the first disinfection information of the banknote with the inferior state of the disinfection. Thus, even in the case where there is a risk that the banknote with the superior state of the disinfection is affected by bacteria or virus adhering on the banknote with the inferior state of the disinfection due to stacking of banknotes in the storage unit, the state of the disinfection of the banknote can be appropriately managed.

The update of the first disinfection information of the first banknote may be performed in the case where the first banknote and the second banknote are in direct contact with each other in the storage unit, i.e., the case where the second banknote is stored in the storage unit immediately after the first banknote. In addition, the update of the first disinfection information of the first banknote may be performed in the case where the number of banknotes interposed between the first banknote and the second banknote is equal to or smaller than a predetermined number, i.e., the case where the number of banknotes that are stored in the storage unit in the period between the storage of the first banknote and the storage of the second banknote is equal to or smaller than a predetermined number. In addition, the update of the first disinfection information of the first banknote may be performed regardless of the number of banknotes interposed between the first banknote and the second banknote.

In the banknote management system according to Embodiment 1, the following banknote management method may also be performed. In this case, the first banknote processing apparatus 10 processes the first banknote and the second banknote as the banknote. In addition, the first banknote processing apparatus 10 includes a storage unit. This storage unit stores a plurality of banknotes in a stacked state. Specifically, the first banknote is stored in the storage unit, and the second banknote is stored in the storage unit in a state where it is stacked on the first banknote.

Figure 4:
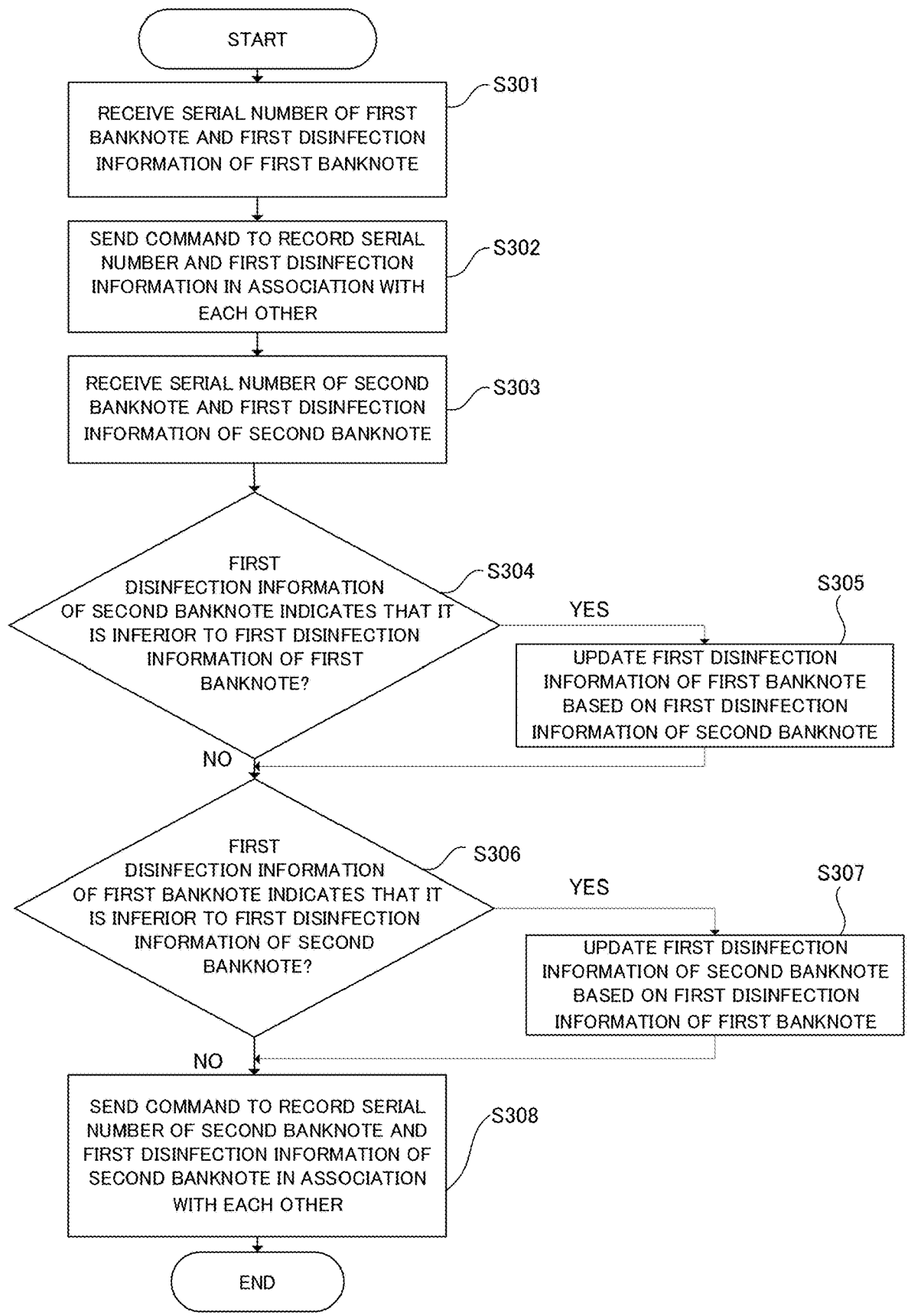
FIG. 4 is a flowchart illustrating the banknote management method in the banknote management system according to Embodiment 1.

FIG. 4 is a flowchart illustrating a banknote management method in the banknote management system 1, especially a step performed by the computer 30. Step S301 to step S305 are identical to step S201 to step S205 in FIG. 3, and therefore the description thereof is omitted.

In the case where the first disinfection information of the second banknote does not indicate that it is inferior to the first disinfection information of the first banknote in terms of the state of the disinfection (S304: NO), and, the case where the first disinfection information of the first banknote is updated (after S305), the computer 30 determines whether the first disinfection information of the first banknote indicates that it is inferior to the first disinfection information of the second banknote in terms of the state of the disinfection (S306).

In the case where the first disinfection information of the first banknote indicates that it is inferior to the first disinfection information of the second banknote in terms of the state of the disinfection (S306: YES), the computer 30 updates the first disinfection information of the second banknote on the basis of the first disinfection information of the first banknote (S307). The update of the first disinfection information of the second banknote may be replacement with the first disinfection information of the first banknote. In addition, the update of the first disinfection information of the second banknote may be an update to information representing the degree of the disinfection between the degree of the disinfection of the first banknote and the degree of the disinfection of the second banknote.

In the case where the first disinfection information of the first banknote does not indicate that it is inferior to the first disinfection information of the second banknote in terms of the state of the disinfection (S306: NO), and the case where the first disinfection information of the second banknote is updated (after S307), the computer 30 sends, to the recording apparatus 40, a command to record the serial number of the second banknote and the first disinfection information of the second banknote or the updated first disinfection information of the second banknote in association with each other (S308).

With the management method described above, in the case where a banknote with the inferior state of the disinfection is stored in the storage unit later or earlier, the first disinfection information of the banknote with the superior state of the disinfection can be updated based on the first disinfection information of the banknote with the inferior state of the disinfection. Thus, even in the case where there is a risk that the banknote with the superior state of the disinfection is affected by bacteria or virus adhering on the banknote with the inferior state of the disinfection due to stacking of banknotes in the storage unit, the state of the disinfection of the banknote can be appropriately managed.

The update of the first disinfection information of the first banknote or the second banknote may be performed in the case where the first banknote and the second banknote are in direct contact with each other in the storage unit, i.e., the case where the second banknote is stored in the storage unit immediately after the first banknote. In addition, the update of the first disinfection information of the first banknote or the second banknote may be performed in the case where the number of banknotes interposed between the first banknote and the second banknote is equal to or smaller than a predetermined number, i.e., the case where the number of banknotes that are stored in the storage unit in the period between the storage of the first banknote and the storage of the second banknote is equal to or smaller than a predetermined number. In addition, the update of the first disinfection information of the first banknote or the second banknote may be performed regardless of the number of banknotes interposed between the first banknote and the second banknote.

Embodiment 2

Figure 5:
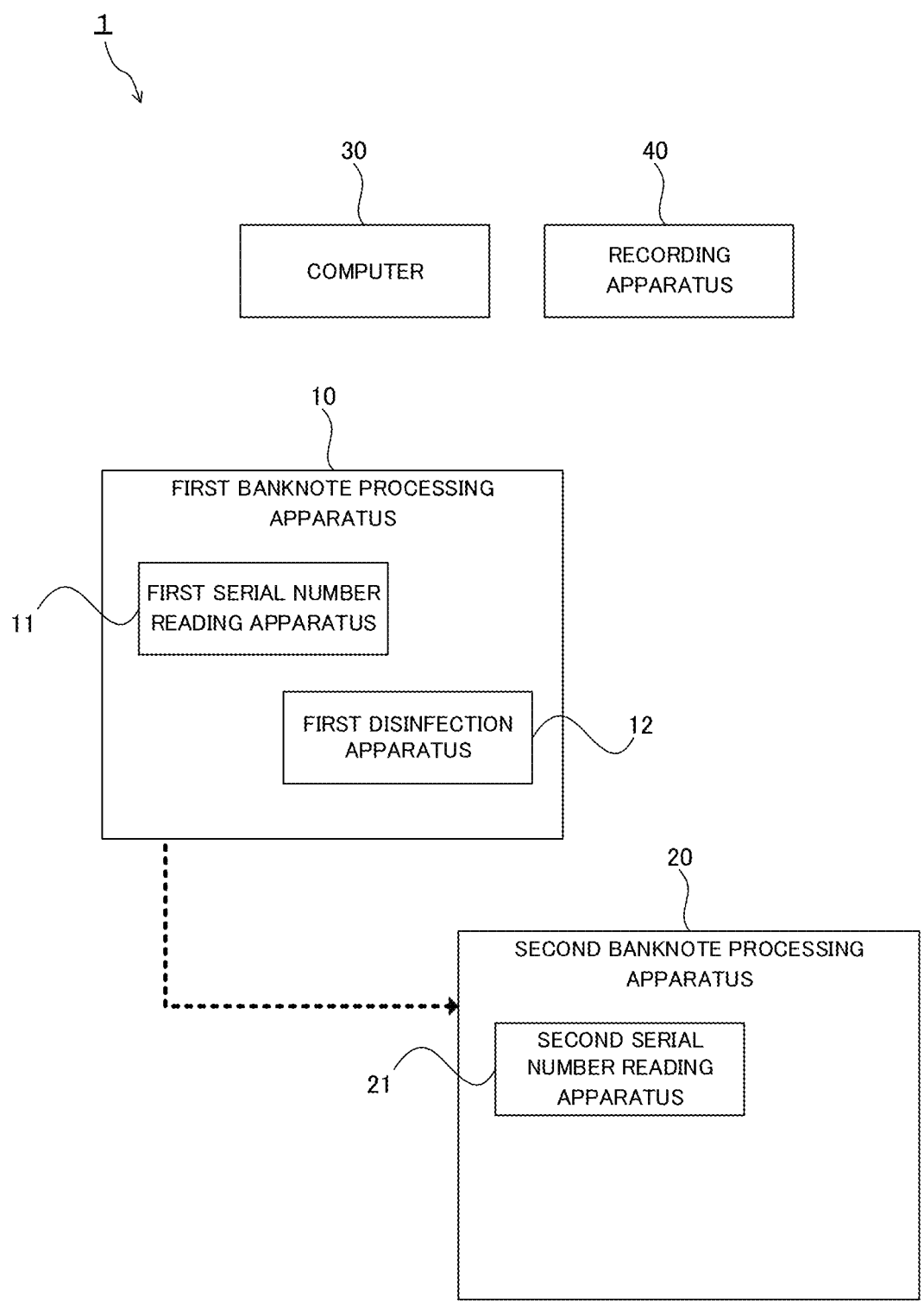
FIG. 5 is a schematic view of a banknote management system according to Embodiment 2.

FIG. 5 is a schematic view of the banknote management system 1 according to Embodiment 2. The banknote management system 1 includes the first banknote processing apparatus 10, a second banknote processing apparatus 20, the computer 30 and the recording apparatus 40. Note that the descriptions overlapping Embodiment 1 may be omitted below.

The second banknote processing apparatus 20 is an apparatus for processing banknotes that is installed in a financial institution such as a bank, a distribution store such as convenience store or a facility such as a security transport institution. Specific examples of it include a banknote coin depositing machine, a banknote coin depositing and dispensing machine, an automatic teller machine, a tax payment machine, a money changer, a teller machine, a ticket vending machine, a vending machine, a change machine, a sales depositing and dispensing machine, a banknote counter, a banknote sorting machine, a banknote recycler, a banknote bundler, an electronic money charging machine, and a banknote disinfection apparatus.

The second banknote processing apparatus 20 may be disposed in the same facility as that of the first banknote processing apparatus 10, or in a facility different from that of the first banknote processing apparatus 10.

The second banknote processing apparatus 20 includes a second serial number reading apparatus 21.

The second serial number reading apparatus 21 reads the serial number from the banknote processed by the second banknote processing apparatus 20. The second serial number reading apparatus 21 may also be a recognition unit that reads the serial number and recognizes the denomination, fitness, authentication and the like of banknotes.

The computer 30 may be a control apparatus of the first banknote processing apparatus 10 provided in the first banknote processing apparatus 10, or a control apparatus of the second banknote processing apparatus 20 provided in the second banknote processing apparatus 20. In addition, the recording apparatus 40 may be a recording apparatus provided in the first banknote processing apparatus 10, or a recording apparatus provided in the second banknote processing apparatus 20. In addition, the recording apparatus 40 may be a recording apparatus provided in the computer 30.

Note that the dotted line in FIG. 5 indicates an exemplary flow of a banknote. In the example illustrated in FIG. 5, the banknote that has been processed by the first banknote processing apparatus 10 is processed by the second banknote processing apparatus 20.

In the banknote management system 1 with the above-described configuration, banknotes are managed in the following manner.

Figure 6:
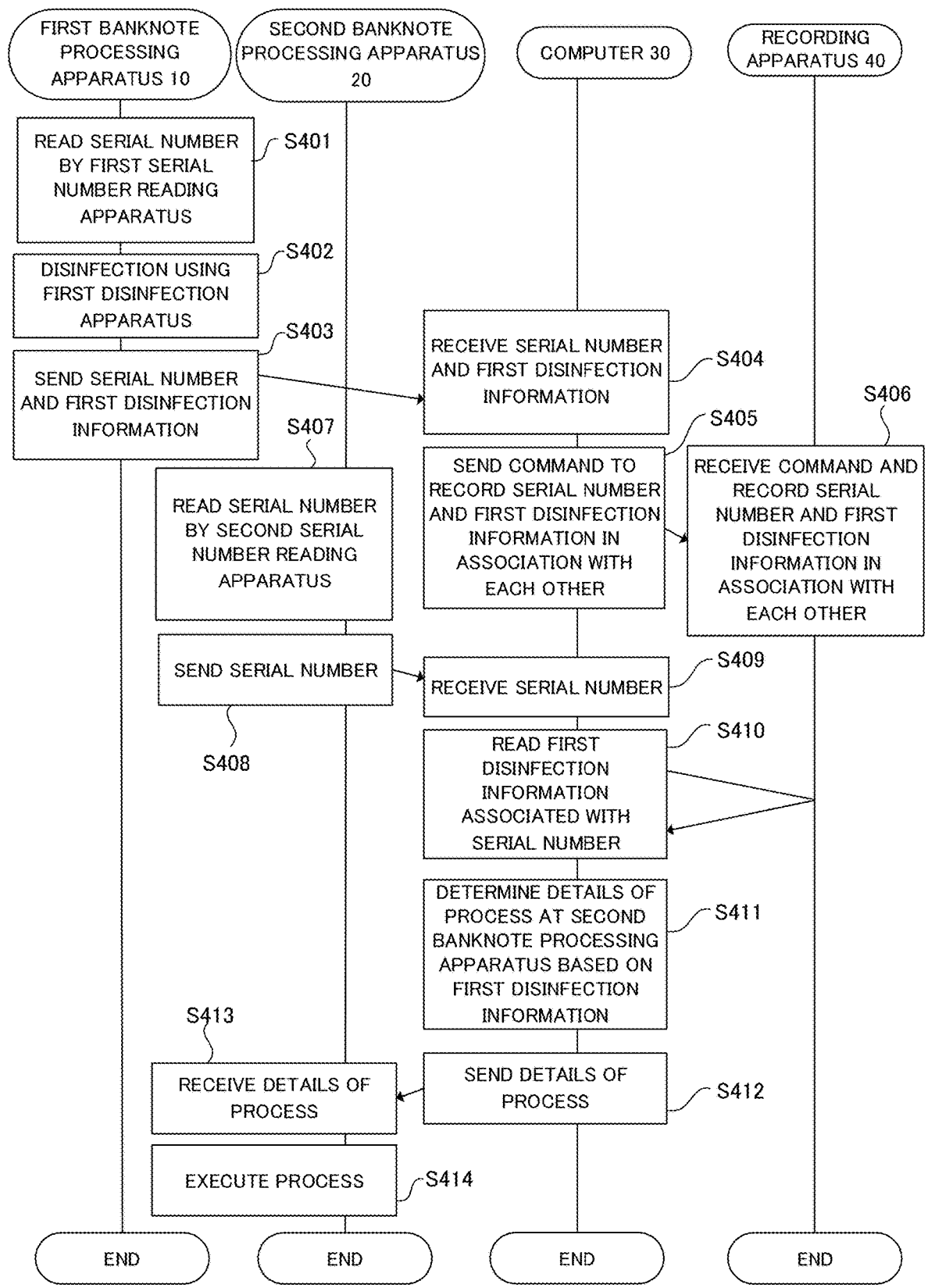
FIG. 6 is a sequence diagram illustrating the banknote management method in the banknote management system according to Embodiment 2.

FIG. 6 is a sequence diagram illustrating a banknote management method in the banknote management system 1.

First, when receiving a banknote to be processed, the first banknote processing apparatus 10 reads the serial number from the banknote by the first serial number reading apparatus 11 (S401). Subsequently, with the first disinfection apparatus 12, the first banknote processing apparatus 10 disinfects the banknote whose serial number has been read (S402). Thereafter, the first banknote processing apparatus 10 sends, to the computer 30, the serial number of this banknote and the first disinfection information of this banknote (S403). At this time, the first banknote processing apparatus 10 sends, to the computer 30, the serial number and the first disinfection information in the state where they are associated with each other. The computer 30 receives the serial number sent from the first banknote processing apparatus 10 (which may be construed as the first serial number reading apparatus 11 and the first disinfection apparatus 12) (S404).

Note that the first banknote processing apparatus 10 may perform the reading of the serial number prior to the disinfection of the banknote, or may perform the disinfection of the banknote prior to the reading of the serial number. In addition, to the computer 30, the first banknote processing apparatus 10 may send the serial number and the first disinfection information at the same time, send the serial number prior to the first disinfection information, or send the first disinfection information prior to the serial number. For example, S403 may branch to the step of sending the serial number and the step of sending the first disinfection information, the step of sending the serial number may be performed between S401 and S402, and the step of sending the first disinfection information may be performed after S402. In this case, naturally, S404 also branches to two steps. Note that when the serial number and the first disinfection information are transmitted and received at different timings, the first banknote processing apparatus 10 may operate in the following manner such that the computer 30 can associate the serial number and the first disinfection information with each other. Specifically, the first banknote processing apparatus 10 may send the serial number and the first disinfection information to the computer 30, with some key information (e.g., the processing time or processing order of banknotes) added to at least one of the serial number and the first disinfection information.

When receiving the serial number and the first disinfection information, the computer 30 sends, to the recording apparatus 40, a command to record the serial number and the first disinfection information in association with each other (S405). Naturally, information representing the serial number and the first disinfection information is included in this command.

When receiving the command from the computer 30, the recording apparatus 40 records the serial number and the first disinfection information in association with each other in accordance with the command (S406).

In addition, when receiving a banknote to be processed, the second banknote processing apparatus 20 reads the serial number from the banknote by the second serial number reading apparatus 21 (S407). Subsequently, the second banknote processing apparatus 20 sends the read serial number to the computer 30 (S408). The computer 30 receives the serial number sent from the second banknote processing apparatus 20 (which may be construed as the second serial number reading apparatus 21) (S409).

Next, the computer 30 reads, from the recording apparatus 40, the first disinfection information that is recorded in association with the serial number that matches the serial number received from the second banknote processing apparatus 20 (S410). Note that the fact that it can read, from the recording apparatus 40, the first disinfection information that is recorded in association with the serial number that matches the serial number received from the second banknote processing apparatus 20 means that as indicated by the dotted line in FIG. 5, the banknote processed by the first banknote processing apparatus 10 is transported to the second banknote processing apparatus 20 by some means, and processed by the second banknote processing apparatus 20. In addition, in the case where the first disinfection information that is recorded in association with the serial number that matches the serial number received from the second banknote processing apparatus 20 cannot be read from the recording apparatus 40, the computer 30 sends, to the recording apparatus 40, a command to record the first disinfection information and the serial number received from the second banknote processing apparatus 20 in association with each other.

Subsequently, the computer 30 determines the details of the process to be performed on the banknote in the second banknote processing apparatus 20 on the basis of the first disinfection information read from the recording apparatus 40 (S411). For example, in the case where the read first disinfection information indicates that the state of the disinfection is superior (e.g., the disinfection has been performed, or the degree of the disinfection is a predetermined level or greater), storing of banknotes in a recyclable storage unit (i.e., a storage unit in which only recyclable banknotes are stored) may be determined as the details of the process. In addition, in the case where it indicates that the state of the disinfection is inferior (e.g., disinfection has not been performed, or the degree of the disinfection is lower than a predetermined level), storing of banknotes in a non-recyclable storage unit (i.e., a storage unit in which non-recyclable banknotes are stored) may be determined as the details of the process. In this manner, while ensuring a large number of recyclable banknotes as much as possible, it is possible to prevent a banknote that is in an inferior state of disinfection and requires care in handling from being ejected in the inferior state of disinfection from the second banknote processing apparatus 20.

In addition, in the case where the second banknote processing apparatus 20 includes a second disinfection apparatus 22 (see FIG. 7), the details of the process may be determined in the following manner. Specifically, in the case where the read first disinfection information indicates that the disinfection has been performed, or that the state of the disinfection is superior (e.g., the degree of the disinfection is greater than a predetermined value), it is possible to determine that no disinfection is to be performed at the second disinfection apparatus 22 as the details of the process. In addition, in the case where it indicates that disinfection has not been performed, or that the state of the disinfection is inferior, it is possible to determine that the disinfection is to be performed at the second disinfection apparatus 22 as the details of the process. In addition, the details of the disinfection (the reliability of the disinfection) performed at the second disinfection apparatus 22 may be determined as the details of the process. In the above-described manner, it is possible to prevent unnecessary consumption of the power or the disinfecting material through execution of disinfection on a banknote that does not require disinfection.

When the details of the process is determined, the computer 30 sends the determined details of process to the second banknote processing apparatus 20 (S412). The second banknote processing apparatus 20 receives the details of the process (S413), and executes the processing on the banknote in accordance with the details (S414).

With the management method described above, appropriate banknote processes, and in turn, smooth banknote processes can be performed in the entire system by sharing information among a plurality of banknote processing apparatuses.

Embodiment 3

Figure 7:
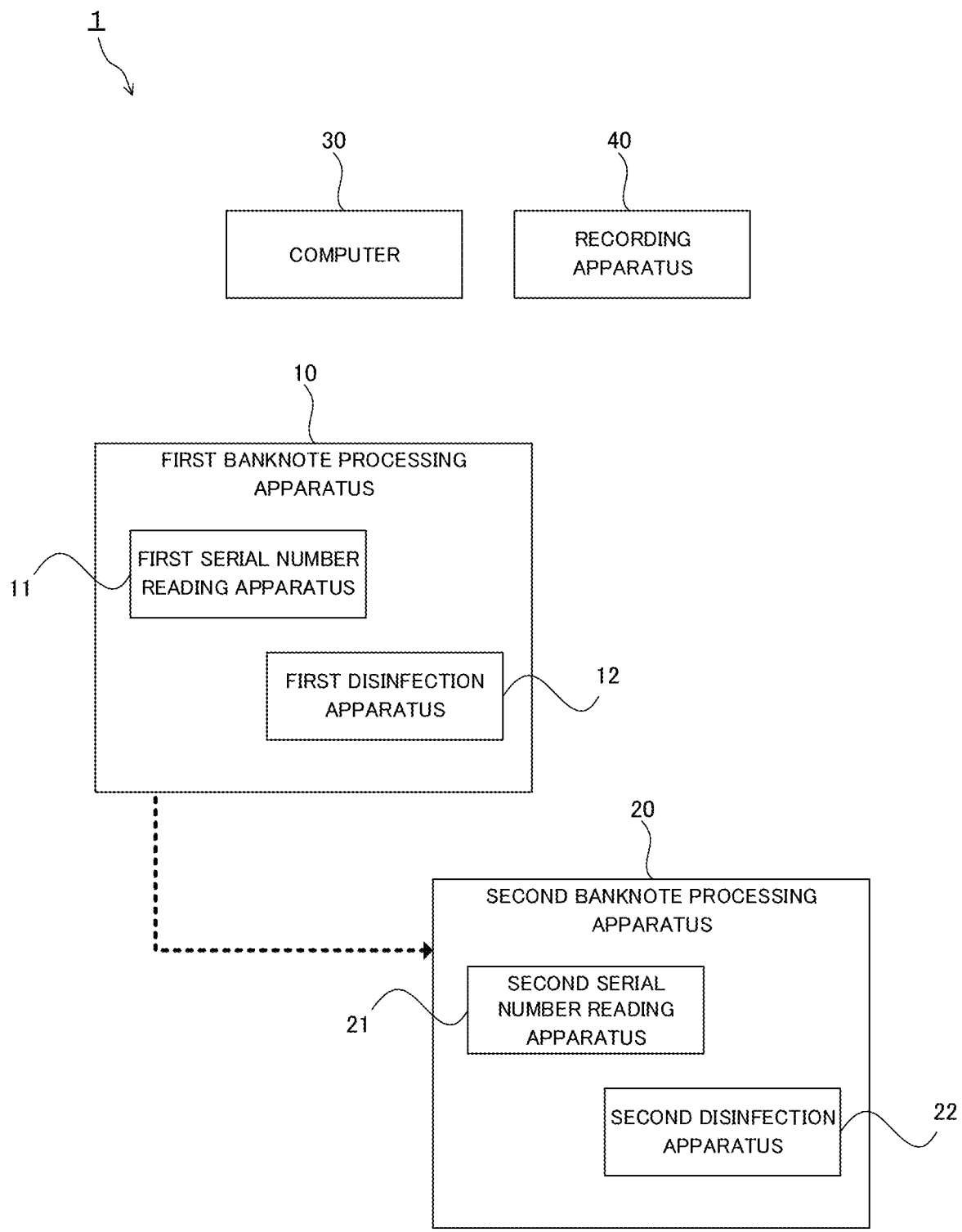
FIG. 7 is a schematic view of a banknote management system according to Embodiment 3.

FIG. 7 is a schematic view of the banknote management system 1 according to Embodiment 3. The banknote management system 1 includes the first banknote processing apparatus 10, the second banknote processing apparatus 20, the computer 30 and the recording apparatus 40. Note that the descriptions overlapping Embodiment 1 or Embodiment 2 may be omitted below.

The second banknote processing apparatus 20 includes the second serial number reading apparatus 21 and the second disinfection apparatus 22.

The second disinfection apparatus 22 disinfects the banknote processed by the second banknote processing apparatus 20. Note that the disinfection of the banknote itself may be the processing of banknotes performed by the second banknote processing apparatus 20. The second disinfection apparatus 22 may include one or more of an ultraviolet ray irradiation apparatus, a disinfection material supply apparatus and a heating apparatus.

The computer 30 is, for example, a server apparatus communicatively connected to the first banknote processing apparatus 10 and the second banknote processing apparatus 20 through a network such as the Internet.

The recording apparatus 40 is, for example, a recording apparatus communicatively connected to the computer 30 through a network such as the Internet.

The computer 30 may be a control apparatus of the first banknote processing apparatus 10 provided in the first banknote processing apparatus 10, or a control apparatus of the second banknote processing apparatus 20 provided in the second banknote processing apparatus 20. In addition, the recording apparatus 40 may be a recording apparatus provided in the first banknote processing apparatus 10, or a recording apparatus provided in the second banknote processing apparatus 20. In addition, the recording apparatus 40 may be a recording apparatus provided in the computer 30.

Note that the dotted line in FIG. 7 indicates an exemplary flow of a banknote. In the example illustrated in FIG. 7, the banknote that has been processed by the first banknote processing apparatus 10 is processed by the second banknote processing apparatus 20.

In the banknote management system 1 with the above-described configuration, banknotes are managed in the following manner.

Figure 8:
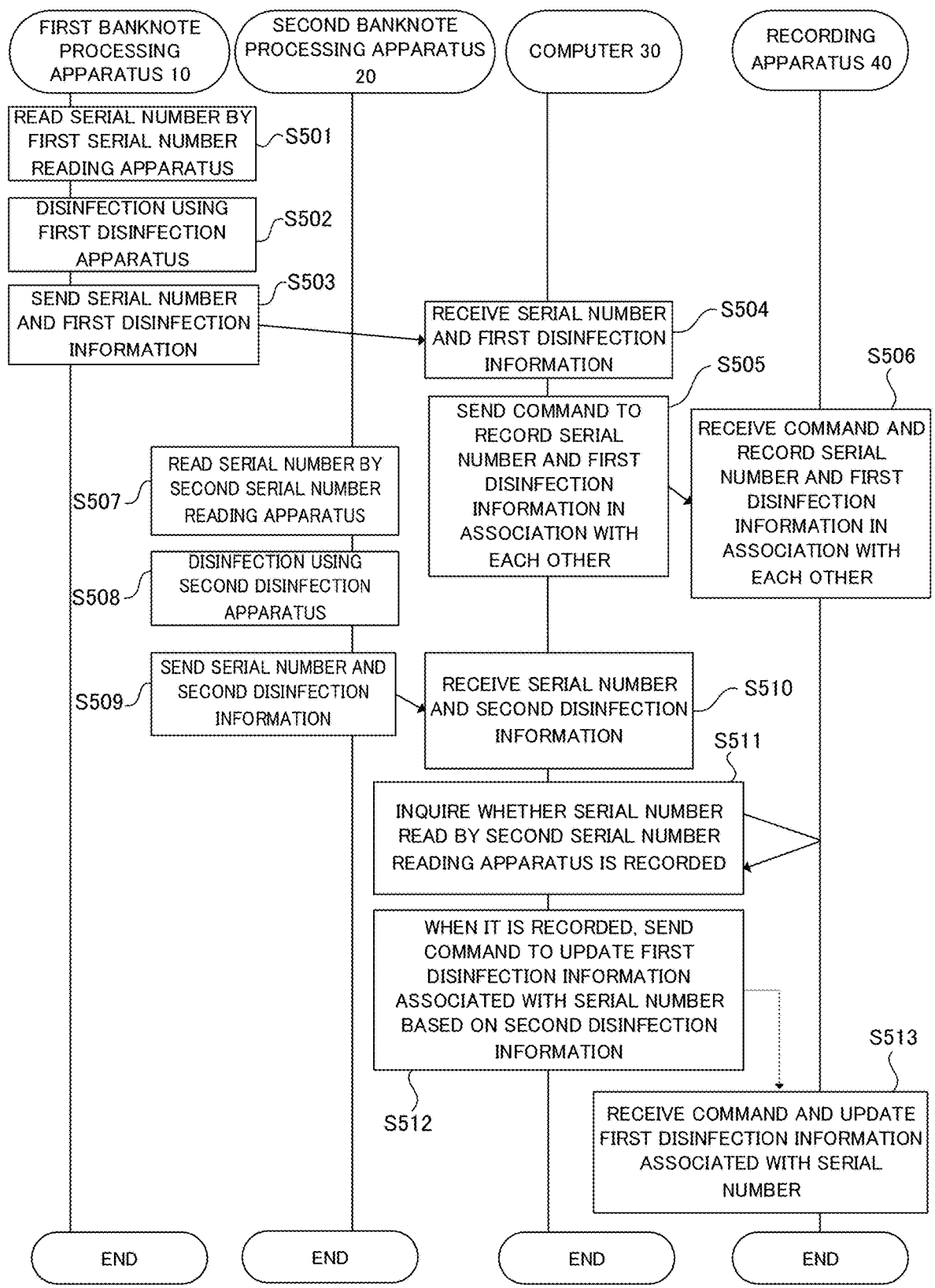
FIG. 8 is a sequence diagram illustrating the banknote management method in the banknote management system according to Embodiment 3.

FIG. 8 is a sequence diagram illustrating a banknote management method in the banknote management system 1. The details of step S501 to step S507 in FIG. 8 are identical to those of step S401 to step S407 in FIG. 6, and therefore the description thereof is omitted.

At step S507, after reading the serial number from the banknote, the second banknote processing apparatus 20 disinfects the banknote whose serial number has been read, by using the second disinfection apparatus 22 (S508). Subsequently, the second banknote processing apparatus 20 sends, to the computer 30, the serial number and second disinfection information (S509). The computer 30 receives the serial number and the second disinfection information sent from the second banknote processing apparatus 20 (which may be construed as the second serial number reading apparatus 21 and the second disinfection apparatus 22) (S510).

Note that the second banknote processing apparatus 20 may perform the reading of the serial number prior to the disinfection of the banknote, or may perform the disinfection of the banknote prior to the reading of the serial number. In addition, the second banknote processing apparatus 20 may send the serial number and the second disinfection information at the same time, send the serial number prior to the second disinfection information, or send the second disinfection information prior to the serial number, to the computer 30. For example, S509 may branch to the step of sending the serial number and the step of sending the second disinfection information, the step of sending the serial number may be performed between S507 and S508, and the step of sending the second disinfection information may be performed after S508. In this case, naturally, S510 also branches to two steps. Note that in the case where the serial number and the second disinfection information are transmitted and received at different timings, the second banknote processing apparatus 20 may operate in the following manner so that the computer 30 can associate the serial number and the second disinfection information with each other. Specifically, the second banknote processing apparatus 20 may send the serial number and the second disinfection information to the computer 30, with some key information (e.g., the processing time or processing order of banknotes) added to at least one of the serial number and the second disinfection information.

When receiving the serial number and the second disinfection information, the computer 30 makes an inquiry of the recording apparatus 40 about whether the serial number of the banknote read by the second serial number reading apparatus 21 is recorded (S511).

In the case where this serial number is recorded in the recording apparatus 40, the computer 30 sends a command to update the first disinfection information recorded in the recording apparatus 40 in association with this serial number on the basis of the second disinfection information (S512). To be more specific, the computer 30 generates new first disinfection information and sends a command, to the recording apparatus 40, to record this new first disinfection information in association with the serial number read by the second serial number reading apparatus 21.

The fact that the serial number of the banknote processed by the second banknote processing apparatus 20 is recorded in the recording apparatus 40 means that this banknote has been disinfected by the second disinfection apparatus 22 of the second banknote processing apparatus 20 after the disinfection at the first disinfection apparatus 12 of the first banknote processing apparatus 10. This means that the disinfection has been performed a plurality of times on this banknote. As such, new first disinfection information (the first disinfection information after the update), which is the update destination, may be set as information representing the degree of the disinfection superior to the degree of the disinfection represented by the second disinfection information and the old first disinfection information (the first disinfection information before the update) as the update source. For example, in the case where the disinfection performed by the first disinfection apparatus 12 has a capability of inactivating 80% of the virus adhering on the banknote, the first disinfection information is a numerical value of 0.8 (maximum value: 1), the disinfection performed by the second disinfection apparatus 22 has a capability of inactivating 70% of the virus adhering on the banknote, and the second disinfection information is a numerical value of 0.7, the new first disinfection information as the update destination may be set as a numerical value of 0.94 (=(1−(1−0.8)×(1−0.7)). Although it is only a simple theoretical calculation, but it shows that 94% of the virus on the banknote is inactivated after two disinfection.

In the case where the state of the disinfection represented by the second disinfection information is superior to the state of the disinfection represented by the first disinfection information of the update source, the new first disinfection information of the update destination may be the second disinfection information itself. In this case, the update of the first disinfection information is replacement with the second disinfection information.

The recording apparatus 40 receiving a command related to an update updates the first disinfection information recorded in association with the serial number read by the second serial number reading apparatus 21, to the new first disinfection information, in accordance with the received command, and records it (S513).

Note that in the case where the computer 30 performs an inquiry of the recording apparatus 40 about whether the serial number of the banknote read by the second serial number reading apparatus 21 is recorded (S511), and the result shows that it is not recorded, the computer 30 sends the following command to the recording apparatus 40. That is, the computer 30 sends, to the recording apparatus 40, a command to record the second disinfection information received from the second banknote processing apparatus 20 as the first disinfection information in association with the serial number received from the second banknote processing apparatus 20.

From S501 to S513 described above are the banknote management method executed by the banknote management system 1 exemplified in FIG. 7.

The following describes a case where the first banknote processing apparatus 10 and the second banknote processing apparatus 20 are sorting machines, and processes S501 to S513 illustrated in FIG. 8 are incorporated in the banknote sorting process of the first banknote processing apparatus 10 and the second banknote processing apparatus 20.

In the case where the first banknote processing apparatus 10 is a banknote sorting machine including five storage units and the second banknote processing apparatus 20 is a banknote sorting machine including five storage units, the first banknote processing apparatus 10 sorts banknotes in the following manner, for example.

(1-1): $1 fit note, (1-2): $1 unfit note, (1-3): $5 fit note, (1-4): $5 unfit note, and (1-5): banknotes other than (1-1) to (1-4).

At this time, for each banknote, the serial number information and the first disinfection information are associated with each other and recorded by the computer 30 and the recording apparatus 40.

In addition, in an example of a sorting operation, information relating to the serial number, denomination, the fitness of the banknote (hereinafter referred to as fitness information) and the first disinfection information are associated with each other and recorded by the computer 30 and the recording apparatus 40.

Subsequently, the second banknote processing apparatus 20 sorts the banknotes of (1-5) (banknotes other than (1-1) to (1-4)) sorted by the first banknote processing apparatus 10 in the following manner, for example.

(2-1): $10 fit note, (2-2): $10 unfit note, (2-3): $20 fit note, (2-4): $20 unfit note, and (2-5): banknotes other than (2-1) to (2-4).

At this time, for each banknote, the serial number information and the first disinfection information updated based on the second disinfection information are associated with each other and recorded by the computer 30 and the recording apparatus 40.

In addition, in an example of an sorting operation, the serial number information, the denomination information, the fitness information, and the first disinfection information updated based on the second disinfection information are associated with each other and recorded by the computer 30 and the recording apparatus 40.

The banknote processed by the second banknote processing apparatus 20 passes through the second disinfection apparatus 22 of the second banknote processing apparatus 20 after passing through the first disinfection apparatus 12 of the first banknote processing apparatus 10. That is, regarding the banknote processed by the second banknote processing apparatus 20, the first disinfection information associated with the serial number of the banknote is updated by the computer 30 based on the second disinfection information (see the process of S513).

With the management method described above, each of the plurality of banknote processing apparatuses disinfects banknotes, and thus the state of the disinfection of the banknote can be changed (updated) to a superior state in the entire system, and, the state of the disinfection of the banknote being changed to a superior state can be tracked. Thus, the state of the disinfection of the banknote can be changed to a more favorable states and can be appropriately managed, and in turn, the banknote process can be smoothly performed. In addition, even when each banknote processing apparatus does not have powerful disinfection function, reliable disinfection can be performed in the entire system. In the case where there is a trade-off between the powerful disinfection function and the time required for the disinfection, smooth banknote processes can be performed without creating bottlenecks in the overall system.

Embodiment 4

Figure 9:
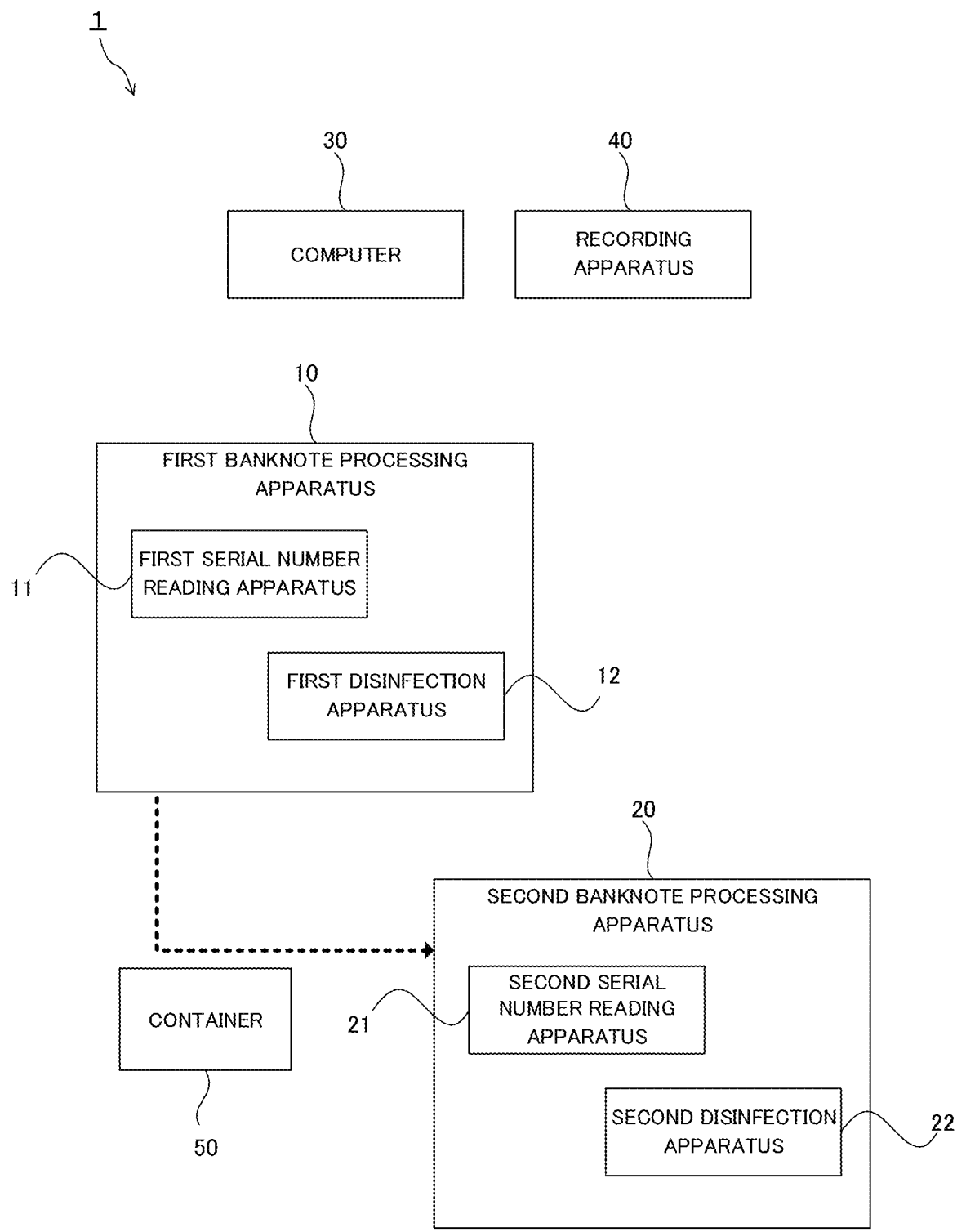
FIG. 9 is a schematic view of a banknote management system according to Embodiment 4.

FIG. 9 is a schematic view of the banknote management system 1 according to Embodiment 4. The banknote management system 1 includes the first banknote processing apparatus 10, the second banknote processing apparatus 20, the computer 30, the recording apparatus 40 and a container 50. Note that the descriptions overlapping Embodiment 1, Embodiment 2 or Embodiment 3 may be omitted below.

The container 50 is a container configured to be detachable to the first banknote processing apparatus 10 and the second banknote processing apparatus 20, and configured to store banknotes in an externally inaccessible manner. The container 50 is, for example, a cassette that stores banknotes in a stacked state, or in a state of being wound between tapes.

The container 50, which is attached to the first banknote processing apparatus 10, receives banknotes processed by the first banknote processing apparatus 10 from the first banknote processing apparatus 10, and stores them in its inside. In addition, after the container 50 is detached from the first banknote processing apparatus 10, the container 50 is attached to the second banknote processing apparatus 20 to pass the banknotes stored inside to the second banknote processing apparatus 20. The second banknote processing apparatus 20 processes the banknotes received from the container 50. The dotted line in FIG. 9 indicates an exemplary flow of the banknote and the container 50.

The banknotes stored in the container 50 can be configured to be externally inaccessible to human's hands. In addition, the banknotes are stored in the container 50 in the state where they are not exposed to the outside of the container 50. A worker or the like who carries banknotes from the first banknote processing apparatus 10 to the second banknote processing apparatus 20 cannot touch the banknote inside the container 50, and therefore the state of the disinfection of banknotes is not affected by a human's touch as long as they are stored in the container 50. Accordingly, at the time of the process at the second banknote processing apparatus 20, the state of the disinfection of the banknote is equal to or greater than that at the time of the process at the first banknote processing apparatus 10. That is, with the banknote management system according to the present embodiment, it is possible to prevent the state of the disinfection of the banknote from being affected when moving banknotes between banknote processing apparatuses.

Accordingly, in the case where the disinfection of a single banknote is repeated a plurality of times at the first banknote processing apparatus 10 and the second banknote processing apparatus 20 as in Embodiment 3, the disinfection of the single banknote is more reliable. That is, the banknote is prevented from being touched by the worker or the like during the repetition of the disinfection of the single banknote, and thus further disinfection can be performed by the second banknote processing apparatus 20 while maintaining the state disinfected by the first banknote processing apparatus 10. In other words, the first disinfection information associated with the serial number of the banknote can be updated to information representing that the state of the disinfection is more superior.

In addition, the recording apparatus 40 may be a recording apparatus installed in the container 50. With this configuration, for example, the serial number and the first disinfection information of the banknote processed by the first banknote processing apparatus 10 can be passed to the second banknote processing apparatus 20 together with the banknote. Thus, the update and management of the first disinfection information can be performed in the second banknote processing apparatus 20 including the computer 30, or through sending information to the computer 30 through the second banknote processing apparatus 20. In addition, the container 50 may include a communication apparatus in addition to the recording apparatus 40. In this case, the recording apparatus 40 can send information to the computer 30 not through the first banknote processing apparatus 10 and the second banknote processing apparatus 20, but through the communication apparatus provided in the container 50 and a network connectable to this communication apparatus. The connection between this communication apparatus and the network may be made in a wireless or wired manner.

Modifications

The present disclosure is not limited to the embodiments described above, and various variations may be added.

For example, on the basis of the first disinfection information recorded in association with the serial number in the recording apparatus 40, the computer 30 in each embodiment may determine an index representing the ease of handling of the banknote with the serial number, and output this index. The index may be, for example, the fee for handling (e.g., conveying) the banknote, the type (which may be construed as category or level) of the material that should be put on or the tool that should be used for handling the banknote. The output may be a display on a screen provided in the computer 30 or the banknote processing apparatus storing the banknote, printing to the paper, or information transmission to the computer used by one that (e.g., the security transport institution) handles the banknote.

An added value can be provided to the disinfected banknote by managing the index in association with the serial number in addition to the first disinfection information for each banknote. Thus, the banknotes can be moved between facilities with an appropriate cost. In addition, it is possible to reassure the user of the first banknote processing apparatus 10 or the second banknote processing apparatus 20 by indicating that the banknote to be provided has been reliably disinfected.

Other Modifications

Other modifications are further described below.

In the case where the first banknote processing apparatus 10 and the second banknote processing apparatus 20 are disposed in the same facility, the transport of banknotes between these apparatuses may be performed through the container 50, or through a transport apparatus or a transport robot that does not require manual operations. In this manner, while maintaining the disinfection state in the first banknote processing apparatus 10, the banknote can be transported to the second banknote processing apparatus 20. In turn, it is possible to prevent deterioration of the state of the disinfection in the course of repetition of processes on the banknote in the same facility.

In addition, the computer 30 may automatically update the first disinfection information in accordance with the time length for which the banknote remains in the first banknote processing apparatus 10 or the second banknote processing apparatus 20. In other words, the computer 30 may change the first disinfection information in such a manner as to indicate that the state of the disinfection is superior over time. For example, in the case where the target virus is known to be inactivated over time, the first disinfection information may be changed to information indicating that the disinfection is in superior condition over time.

Note that in the case where the banknote is ejected from the first banknote processing apparatus 10 or the second banknote processing apparatus 20 in the state where it can be directly touched by the worker or the user, the first banknote processing apparatus 10 or the second banknote processing apparatus 20 may send a predetermined signal to the computer 30. The predetermined signal is a signal that indicates an ejection of a banknote in a directly touchable state and the serial number of the banknote. When receiving this signal, the computer 30 can send, to the recording apparatus 40, a command to erase the first disinfection information recorded in association with the serial number of the banknote, or update it to information indicating that the disinfection has not been made. In this manner, the state of the disinfection of the banknote can be appropriately managed in a state closer to the actual state.

In addition, the first disinfection information may be an index associated with the residual quantity or activity of the bacteria or virus adhering on the banknote. When the first disinfection information is set to these indexes, it is possible to determine how to handle the banknotes in accordance with the actual state. Note that these indexes may be experimentally determined in advance for each of disinfection methods and disinfection details.

Figure 10:
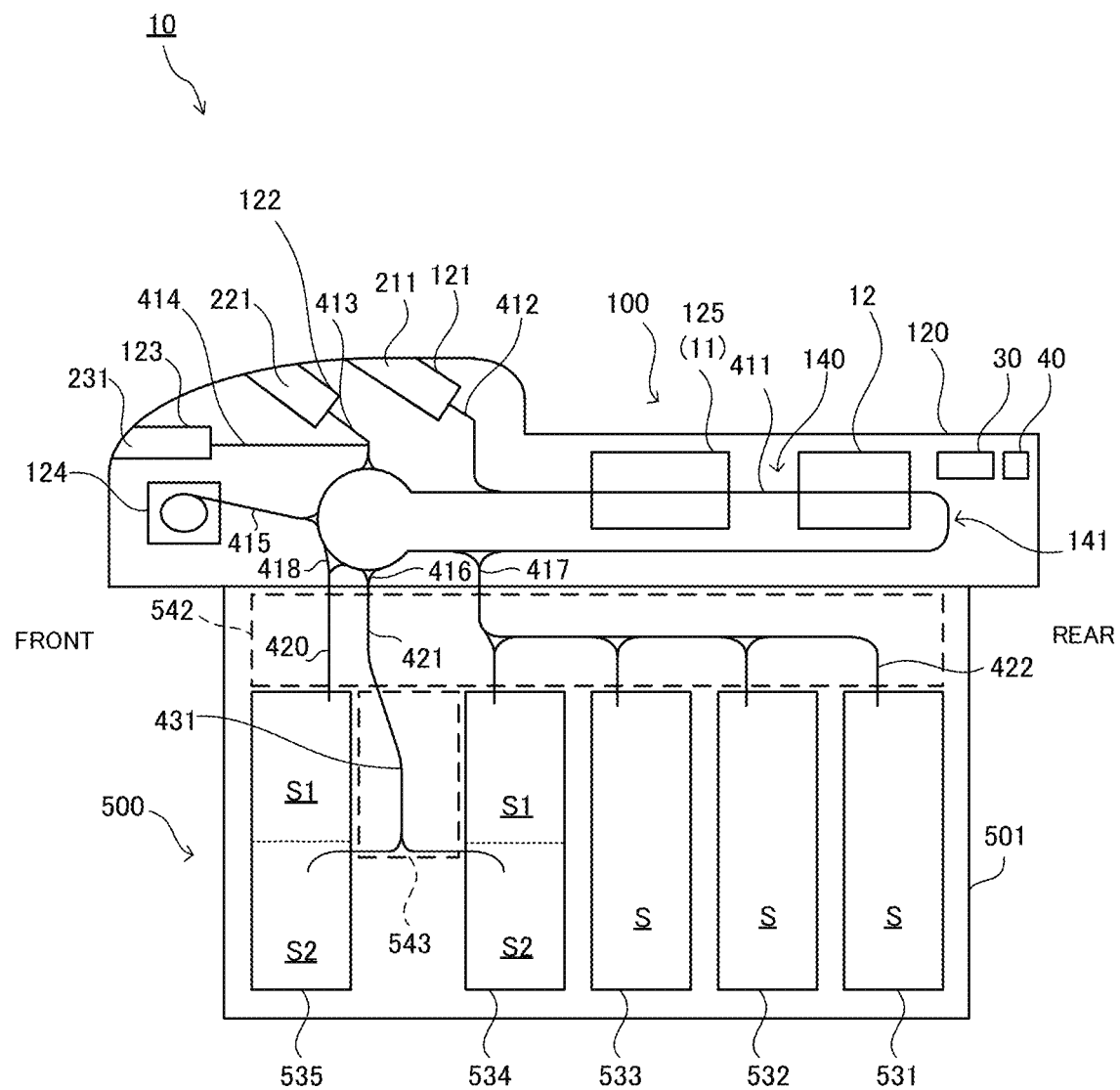
FIG. 10 is a schematic view illustrating an internal structure of a banknote recycler.

In addition, the first banknote processing apparatus 10 may be a banknote recycler. FIG. 10 is a schematic view illustrating an internal structure of the first banknote processing apparatus 10 serving as a banknote recycler. In the following description, the front or forward is the side on which an inlet 211 and an outlet 221 described later are formed, and the rear or rearward is the side opposite to the front or forward. Note that the first banknote processing apparatus 10 serving as the banknote recycler illustrated in FIG. 10 independently makes up the banknote management system 1 of FIG. 1C.

The first banknote processing apparatus 10 performs a process on a banknote. The first banknote processing apparatus 10 includes a processing unit 100 on the upper side, and a safe unit 500 on the lower side. The processing unit 100 includes an upper housing 120, a deposit unit 121 disposed inside the upper housing 120, a dispense unit 122, a reject unit 123, a temporary storage unit 124, a recognition unit 125, the first disinfection apparatus 12, an upper transport unit 141, the computer 30, and the recording apparatus 40.

The safe unit 500 is composed of a safe housing 501. In the safe housing 501, a plurality of storage apparatuses 531 to 535, a lower transport unit 542 and a second lower transport unit 543 are disposed.

The deposit unit 121 is, for example, a portion where the banknote to be deposited is inserted during the deposit process. In addition, the deposit unit 121 may be a portion where the banknote to be counted is inserted during the counting process. The deposit unit 121 includes the inlet 211. The inlet 211 opens upward at the front part of the upper housing 120. The operator puts a banknote into the deposit unit 121 through the inlet 211, by hand. The deposit unit 121 includes a mechanism for taking banknotes into the first banknote processing apparatus 10 one by one.

The dispense unit 122 is a portion to which the banknote sent out from the storage apparatuses 531 to 535 is transported during the dispensing process, for example. In addition, the dispense unit 122 is used also as a portion to which the rejected banknote generated during the deposit process is transported. In addition, the dispense unit 122 is used also as a portion to which a normal banknote counted during the counting process is transported. The dispense unit 122 can hold a plurality of banknotes in a stacked state. The dispense unit 122 includes the outlet 221. The outlet 221 opens upward at a position in front of the inlet 211. The operator can take out the banknotes accumulated in the dispense unit 122 by hand through the outlet 221.

The reject unit 123 is a portion to which the rejected banknote generated during the counting process is transported, for example. The reject unit 123 is disposed at a front part in the upper housing 120. The reject unit 123 is configured to hold a plurality of banknotes in a stacked state. The reject unit 123 includes a second outlet 231. The second outlet 231 opens forward at the front part of the upper housing 120.

The temporary storage unit 124 temporarily stores the banknote to be deposited during the deposit process, for example. The temporary storage unit 124 can send out the stored banknotes. The temporary storage unit 124 is a tape-type storage unit. The temporary storage unit 124 stores banknotes by winding up the banknote around the drum together with the tape.

The recognition unit 125 is disposed at a first transport path 411. The recognition unit 125 acquires at least the serial number of each banknote transported along the first transport path 411. That is, the recognition unit 125 functions as the first serial number reading apparatus 11. In addition, the recognition unit 125 also can recognize the authentication, denomination and fitness.

The first disinfection apparatus 12 is disposed at the first transport path 411.

The computer 30 is a control apparatus of the first banknote processing apparatus 10, and entirely controls the first banknote processing apparatus 10. The recording apparatus 40 records programs executed by the computer 30, the serial number of the processed banknote, the first disinfection information of that banknote and the like.

In the example illustrated in FIG. 10, the first banknote processing apparatus 10 includes the five storage apparatuses 531 to 535. In the following description, the five storage apparatuses may be referred to as the first storage apparatus 531, the second storage apparatus 532, the third storage apparatus 533, the fourth storage apparatus 534, and the fifth storage apparatus 535.

Each of the first the storage apparatus 531, the second storage apparatus 532, and the third storage apparatus 533 includes one storage unit S. Each of the fourth storage apparatus 534 and the fifth storage apparatus 535 includes two storage units (a first storage unit S1 and a second storage unit S2).

Each storage unit S, each first storage unit S1 and each second storage unit S2 includes a transport mechanism. The transport mechanism inputs the banknote into the storage apparatuses 531 to 535 from the outside, and sends out the banknote from the inside of the storage apparatuses 531 to 535 to the outside.

The upper transport unit 141, the lower transport unit 542 and the second lower transport unit 543 make up a transport unit 140. The transport unit 140 transports banknotes one by one with an appropriate interval between each banknote in the first banknote processing apparatus 10.

The upper transport unit 141 includes the first transport path 411, a second transport path 412, a third transport path 413, a fourth transport path 414, a fifth transport path 415, a sixth transport path 416, a seventh transport path 417, and an eighth transport path 418.

Note that in the upper wall that makes up the safe housing 501, three transport paths are formed to extend through it in the vertical direction. The three transport paths are disposed side by side in the front-rear direction. One of the three transport paths connects the sixth transport path 416 and a ninth transport path 421. In addition, another transport path connects the seventh transport path 417 and a tenth transport path 422. In addition, another transport path connects the eighth transport path 418 and an eleventh transport path 420.

The first transport path 411 is configured in a loop form. The transport unit 140 can transport the banknote along the first transport path 411 in the clockwise direction and the counterclockwise direction in FIG. 10.

The second transport path 412 connects the deposit unit 121 and the first transport path 411 to each other. The second transport path 412 transports the banknote from the deposit unit 121 toward the first transport path 411.

The third transport path 413 connects the dispense unit 122 and the first transport path 411 to each other. The third transport path 413 transports the banknote from the first transport path 411 toward the dispense unit 122.

The fourth transport path 414 connects the reject unit 123 and the first transport path 411 to each other. The fourth transport path 414 transports the banknote from the first transport path 411 toward the reject unit 123.

The fifth transport path 415 connects the temporary storage unit 124 and the first transport path 411 to each other. The fifth transport path 415 transports the banknote from the first transport path 411 toward the temporary storage unit 124, and transports the banknote from the temporary storage unit 124 toward the first transport path 411.

The sixth transport path 416 connects the lower transport unit 542 and the first transport path 411 to each other. The sixth transport path 416 transports the banknote from the first transport path 411 toward the lower transport unit 542, and transports the banknote from the lower transport unit 542 toward the first transport path 411.

The seventh transport path 417 connects the lower transport unit 542 and the first transport path 411 to each other. The seventh transport path 417 transports the banknote from the first transport path 411 toward the lower transport unit 542, and transports the banknote from the lower transport unit 542 toward the first transport path 411.

The lower transport unit 542 includes the ninth transport path 421, the tenth transport path 422, and the eleventh transport path 420.

The ninth transport path 421 connects the second lower transport unit 543 and the sixth transport path 416 to each other. The ninth transport path 421 transports the banknote from the sixth transport path 416 toward the second lower transport unit 543, and transports the banknote from the second lower transport unit 543 toward the sixth transport path 416.

The tenth transport path 422 connects the storage unit S of each of the first the storage apparatus 531, the second storage apparatus 532, and the third storage apparatus 533, and the seventh transport path 417 to each other. The tenth transport path 422 transports the banknote from the seventh transport path 417 toward each of the storage apparatuses 531 to 533, and transports the banknote from each of the storage apparatuses 531 to 533 toward the seventh transport path 417.

The eleventh transport path 420 connects the first storage unit S1 of the fifth storage apparatus 535 and the eighth transport path 418 to each other. The eleventh transport path 420 transports the banknote from the eighth transport path 418 toward the fifth storage apparatus 535, and transports the banknote from the fifth storage apparatus 535 toward the eighth transport path 418.

The second lower transport unit 543 is diverged in the middle portion so as to be connected with the second storage unit S2 of the fourth storage apparatus 534 and the second storage unit S2 of the fifth storage apparatus 535. The second lower transport unit 543 transports the banknote from the first transport path 411 toward the second storage unit S2 of the fourth storage apparatus 534, and transports the banknote from this second storage unit S2 toward the first transport path 411. In addition, the second lower transport unit 543 transports the banknote from the first transport path 411 toward the second storage unit S2 of the fifth storage apparatus 535, and transports the banknote from this second storage unit S2 toward the first transport path 411.

In one aspect, a passage sensor that detects passage of banknotes is disposed in each unit of the transport unit 140. When receiving a command from the computer 30, the transport unit 140 transports the banknote to a predetermined transport destination on the basis of a detection signal of the passage sensor. In addition, on the basis of the recognition result of the recognition unit 125, the operation state of the first disinfection apparatus 12, and the detection signal of the passage sensor, the computer 30 acquires the serial number and the first disinfection information of the banknote stored in each storage unit, and records the serial number and the first disinfection information in association with each other in the recording apparatus 40.

In the first banknote processing apparatus 10 configured in the above-described manner as a banknote recycler, banknotes are processed in the following manner, for example.

(1) Deposit Process

A banknote placed at the deposit unit 121 is transported to the recognition unit 125 by the transport unit 140, and recognized. At this time, various information including the serial number is acquired, and the acquired information is sent to the computer (control apparatus) 30. Subsequently, this banknote is transported to the first disinfection apparatus 12 by the transport unit 140, and disinfected. Subsequently, this banknote is transported to the temporary storage unit 124, and temporarily held.

Meanwhile, the first disinfection information is sent to the computer 30. The computer 30 records the first disinfection information and various information including the serial number of this banknote in association with each other in the recording apparatus 40.

The computer 30 determines the storage apparatus for storing each banknote among the storage apparatuses 531 to 535 in accordance with the recognition result of each banknote. When all banknotes that should be taken from the deposit unit 121 are held in the temporary storage unit 124, the computer 30 controls the temporary storage unit 124, the transport unit 140 and the storage apparatuses 531 to 535 to transport each banknote to the storage apparatuses 531 to 535 determined to be a transport destination.

That is, the banknote placed at the deposit unit 121 is disinfected once, and then stored in any one of the storage apparatuses 531 to 535. In addition, information indicating that it has been disinfected once is recorded in association with the serial number in the recording apparatus 40. Note that the banknote taken from the deposit unit 121 may be transported to the storage apparatuses 531 to 535 determined in accordance with the recognition result after the single disinfection at the first disinfection apparatus 12, without being temporarily held in the temporary storage unit 124.

During the transportation to the storage apparatuses 531 to 535 as the storage destination, the banknote sent out from the temporary storage unit 124 may again pass through the first disinfection apparatus 12 and subjected to the second disinfection.

In addition, the information associated with the serial number may be the number of times of the disinfection at the first disinfection apparatus 12 in the period until it is output from the first banknote processing apparatus 10 after it is taken in the first banknote processing apparatus 10. In addition, in the case where one banknote is disinfected by the first disinfection apparatus 12 a plurality of times, the first disinfection information may be updated to information representing that the state of the disinfection is more superior each time when the disinfection is repeated.

Note that in the case where as the banknote that should be rejected for deposit (so-called rejected banknote) is generated as a result of the recognition process performed during the deposit process, such a banknote may be processed in the following manner, rather than transporting it directly to the reject unit 123. Specifically, it may be temporarily stored in the temporary storage unit 124 after the disinfection at the first disinfection apparatus 12, and then transported to the reject unit 123 after the completion of the processing for the banknote that should be deposited after the re-disinfection at the first disinfection apparatus 12. This can increase the degree of the disinfection of the rejected banknote that is immediately returned to the user of the first banknote processing apparatus 10. During the re-disinfection at the first disinfection apparatus 12, the transport speed of the rejected banknote at the transport unit 140 may be reduced so as to more carefully perform the disinfection.

(2) Reconciliation Process

The reconciliation process is a process of determining (confirming) the amount of banknotes in the storage apparatuses 531 to 535 by sending out the banknote stored in the storage apparatuses 531 to 535 and recognizing it at the recognition unit 125. The banknote disinfection associated with the reconciliation process may be performed.

The banknote stored in the storage apparatuses 531 to 535 is transported to the first disinfection apparatus 12 by the transport unit 140, and disinfected. Subsequently, this banknote is transported to the recognition unit 125 by the transport unit 140, and recognized. At this time, various information including the serial number is acquired, and the acquired information is sent to the computer 30. Subsequently, this banknote is transported to the temporary storage unit 124, and temporarily held.

Meanwhile, the first disinfection information is sent to the computer 30. The computer 30 records the first disinfection information and various information including the serial number of this banknote in association with each other in the recording apparatus 40. At this time, the computer 30 may update the first disinfection information recorded in association with the serial number in the recording apparatus 40 during the deposit process, on the basis of the disinfection performed during the reconciliation process.

When all banknotes that should be temporarily stored in the temporary storage unit 124 are held in the temporary storage unit 124, the computer 30 controls the temporary storage unit 124, the transport unit 140 and the storage apparatuses 531 to 535 to transport each banknote to the original storage apparatuses 531 to 535 or other storage apparatuses 531 to 535.

Specifically, the banknote sent out from the storage apparatuses 531 to 535 is disinfected once, and then again stored in the original or other storage apparatuses 531 to 535. In addition, information indicating that the disinfection has been performed by the sum of the number of times of the disinfection performed during the deposit process and the number of times of the disinfection performed during the reconciliation process is recorded in association with the serial number in the recording apparatus 40. Through the reconciliation process described above, the disinfection of the banknote can be performed while performing the reconciliation process, it is not necessary to transport the banknote only for the disinfection, and thus efficient banknote processes can be performed.

During the transportation to the storage apparatuses 531 to 535 as the storage destination, the banknote sent out from the temporary storage unit 124 may again pass through the first disinfection apparatus 12 and subjected to the second disinfection in the reconciliation process.

(3) Dispensing Process

The banknotes stored in the storage apparatuses 531 to 535 are sent out to the transport unit 140 in accordance with a dispense request input to the first banknote processing apparatus 10. The sent banknote is transported to the first disinfection apparatus 12 by the transport unit 140, and disinfected. Subsequently, this banknote is transported to the recognition unit 125 by the transport unit 140, and recognized. At this time, various information including the serial number is acquired, and the acquired information is sent to the computer 30. Subsequently, this banknote is transported to the temporary storage unit 124, and temporarily held.

Meanwhile, the first disinfection information is sent to the computer 30. The computer 30 records the first disinfection information and various information including the serial number of this banknote in association with each other in the recording apparatus 40. At this time, the computer 30 may update the first disinfection information recorded in association with the serial number in the recording apparatus 40 during the deposit process or the reconciliation process, on the basis of the disinfection performed during the dispensing process.

When all banknotes that should be dispensed are temporarily stored in the temporary storage unit 124, the computer 30 controls the temporary storage unit 124, the transport unit 140 and the dispense unit 122 to transport, from the temporary storage unit 124 to the dispense unit 122, the banknote that should be dispensed.

Specifically, the banknote sent out from the storage apparatuses 531 to 535 is disinfected once, and then dispensed from the dispense unit 122. In addition, information indicating that it has been disinfected once is recorded in association with the serial number in the recording apparatus 40. Note that the banknote taken from the deposit unit 121 may be transported to the dispense unit 122 after the single disinfection at the first disinfection apparatus 12 without being temporarily held in the temporary storage unit 124.

Note that in the case where the state of the disinfection of the dispensed banknote (the first disinfection information) meets a predetermined standard, such as a case where disinfection has been performed for a predetermined number of times or more in the first banknote processing apparatus 10, the first disinfection apparatus 12 need not disinfect the banknote during the dispensing process. The power consumption can be reduced by performing the control of turning off the power of the first disinfection apparatus 12 when it is not necessary to perform disinfection.

In addition, the computer 30 may select a banknote whose state of the disinfection of the banknote meets a predetermined standard, as the banknote that should be dispensed. For example, by preliminarily setting three or more disinfections in the first banknote processing apparatus 10 as a condition as a banknote that can be dispensed, it is possible to prevent dispense of a banknote that is disinfected two times or less than two times in the period between the deposit and the dispense. In this case, for example, the number of times of disinfection may be increased by performing the reconciliation process at night so as to increase the banknote that can be dispensed. The reconciliation process may be performed a plurality of times on a single banknote to increase the number of times of the disinfection.

In addition, to meet a predetermined standard of the disinfection state of the banknote without increasing the number of times of the disinfection, the speed of the transport of the banknote by the transport unit 140 may be reduced than the typical deposit process, reconciliation process or dispensing process in the disinfection of the banknote during the deposit process, reconciliation process or dispensing process. By reducing the transport speed, the passing time at the first disinfection apparatus 12 can be increased, and in turn, the disinfection can be performed more carefully by the first disinfection apparatus 12. That is, a more superior state of the disinfection of the banknote can be set without increasing the number of times of the disinfection.

In addition, during the deposit process or the reconciliation process, the transport destination of the banknote may be selected in accordance with the state of the disinfection. Specifically, banknotes may be stored in different storage apparatuses in the storage apparatuses 531 to 535 depending on whether the state of the disinfection (e.g., the number of times of disinfection) is greater than a predetermined condition (the number of times).

In addition, during the reconciliation process or the dispensing process, whether the disinfection is performed by the first disinfection apparatus 12 may be determined in accordance with the disinfection state of each banknote. That is, it is possible to prevent the unnecessary consumption of the power and the disinfecting material due to further disinfection of banknotes with a superior state of the disinfection, and in addition, the service life of the first disinfection apparatus 12 can be increased.

Figure 11:
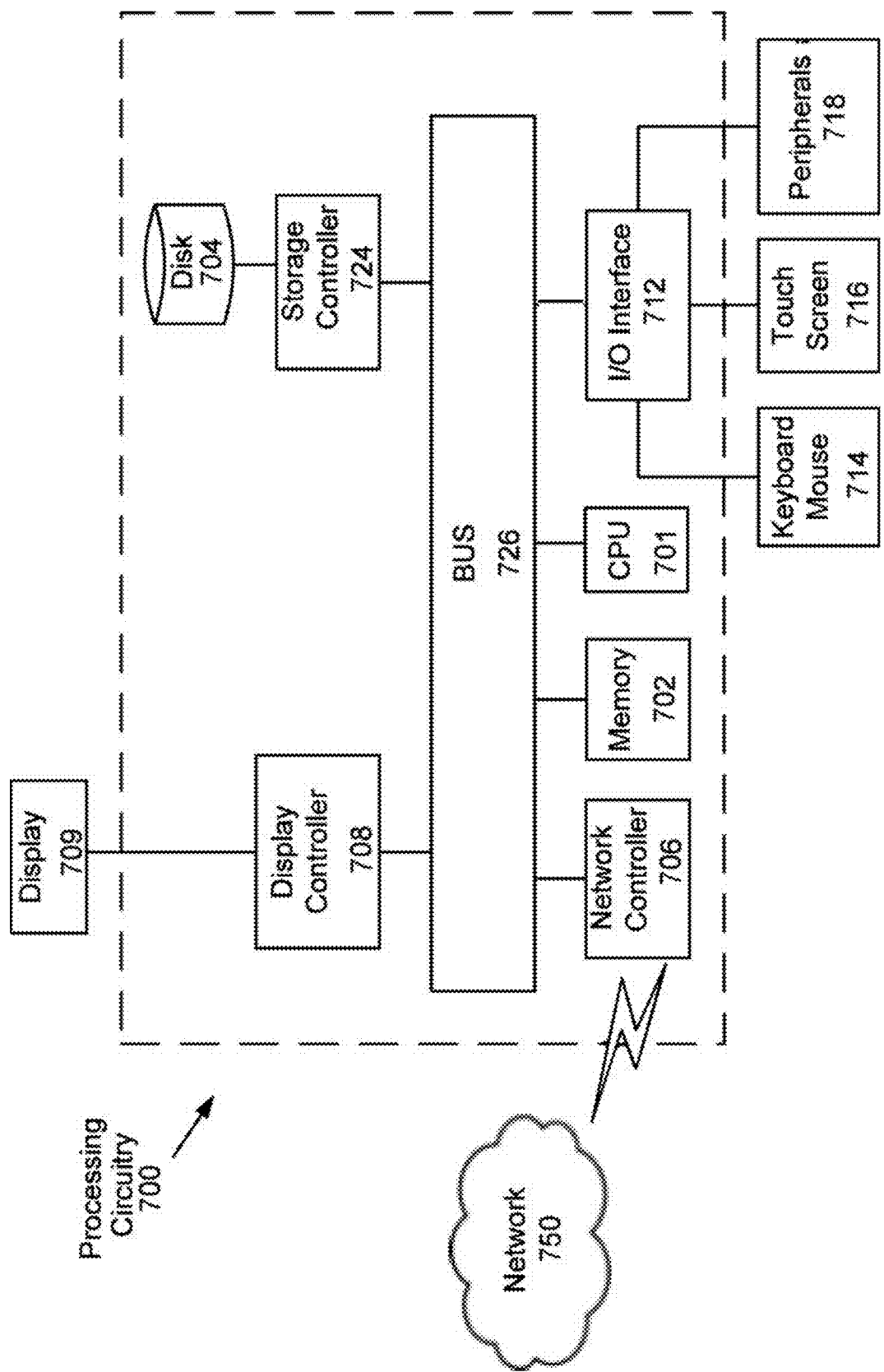
FIG. 11 is a block diagram of processing circuitry that performs computer-based operations in accordance with the present disclosure.

FIG. 11 is a block diagram of processing circuitry that performs computer-based operations in accordance with the present disclosure. FIG. 11 illustrates processing circuitry 700 which is included in or encompasses the computer 30. Alternatively, or additionally, the processing circuitry 700 is included in or encompasses the control apparatus of the first banknote processing apparatus and/or the second banknote processing apparatus.

Processing circuitry 700 is used to control any computer-based and cloud-based control processes, descriptions or blocks in flowcharts can be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The functionality of the elements disclosed herein may be implemented using circuitry or processing circuitry which may include general purpose processors, special purpose processors, integrated circuits, ASICs ("Application Specific Integrated Circuits"), conventional circuitry and/or combinations thereof which are configured or programmed to perform the disclosed functionality. Processors are processing circuitry or circuitry as they include transistors and other circuitry therein. The processor may be a programmed processor which executes a program stored in a memory. In the disclosure, the processing circuitry, units, or means are hardware that carry out or are programmed to perform the recited functionality. The hardware may be any hardware disclosed herein or otherwise known which is programmed or configured to carry out the recited functionality.

In FIG. 11, the processing circuitry 700 includes a CPU 701 which performs one or more of the control processes discussed in this disclosure. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other non-transitory computer readable medium of an information processing device with which the processing circuitry 700 communicates, such as a server or computer. The processes may also be stored in network based storage, cloud-based storage or other mobile accessible storage and executable by processing circuitry 700.

Further, the claimed advancements may be provided as a utility application, background daemon, or component of an operating system, or combination thereof, executing in conjunction with CPU 701 and an operating system such as Microsoft Windows, UNIX, Solaris, LINUX, Apple MAC-OS, Apple iOS and other systems known to those skilled in the art.

The hardware elements in order to achieve the processing circuitry 700 may be realized by various circuitry elements. Further, each of the functions of the above described embodiments may be implemented by circuitry, which includes one or more processing circuits. A processing circuit includes a particularly programmed processor, for example, processor (CPU) 701, as shown in FIG. 11. A processing circuit also includes devices such as an application specific integrated circuit (ASIC) and conventional circuit components arranged to perform the recited functions.

In FIG. 11, the processing circuitry 700 may be a computer or a particular, special-purpose machine. Processing circuitry 700 is programmed to execute processing to control terminal device 10/server device 20.

Alternatively, or additionally, the CPU 701 may be implemented on an FPGA, ASIC, PLD or using discrete logic circuits, as one of ordinary skill in the art would recognize. Further, CPU 701 may be implemented as multiple processors cooperatively working in parallel to perform the instructions of the inventive processes described above. The processing circuitry 700 in FIG. 11 also includes a network controller 706, such as an Ethernet PRO network interface card, for interfacing with network 750. As can be appreciated, the network 750 can be a public network, such as the Internet, or a private network such as a local area network (LAN) or wide area network (WAN), or any combination thereof and can also include Public Switched Telephone Network (PSTN) or Integrated Services Digital Network (ISDN) sub-networks. The network 750 can also be wired, such as an Ethernet network, universal serial bus (USB) cable, or can be wireless such as a cellular network including EDGE, 3G and 4G wireless cellular systems. The wireless network can also be Wi-Fi, wireless LAN, Bluetooth, or any other wireless form of communication that is known. Additionally, network controller 706 may be compliant with other direct communication standards, such as Bluetooth, a near field communication (NFC), infrared ray or other.

The processing circuitry 700 further includes a display controller 708, such as a graphics card or graphics adaptor for interfacing with display 709, such as a monitor. An I/O interface 712 interfaces with a keyboard and/or mouse 714 as well as a touch screen panel 716 on or separate from display 709. I/O interface 712 also connects to a variety of peripherals 718.

The storage controller 724 connects the storage medium disk 704 with communication bus 726, which may be an ISA, EISA, VESA, PCI, or similar, for interconnecting all of the components of the processing circuitry 700. A description of the general features and functionality of the display 709, keyboard and/or mouse 714, as well as the display controller 708, storage controller 724, network controller 706, and I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

INDUSTRIAL APPLICABILITY

The present disclosure is useful for a banknote management system built by linking banknote processing apparatuses used in distribution, finance, and various other industrial fields within or across those fields, or for a banknote management method used in the banknote management system.

The invention claimed is:
1. A banknote management method performed by a computer, the method comprising:

receiving a serial number of a banknote and first disinfection information that is information relating to a state of disinfection of the banknote, the banknote whose serial number has been read in a banknote processing apparatus being disinfected in the banknote processing apparatus;

recording the serial number and the first disinfection information in association with each other in a recording apparatus; and associating the state of disinfection of each banknote processed by the banknote processing apparatus with the serial number.

2. The banknote management method according to claim 1, wherein the first disinfection information is information representing whether the banknote has been disinfected.

3. The banknote management method according to claim 1, wherein the first disinfection information is information representing a degree of disinfection of the banknote.

4. The banknote management method according to claim 1,
wherein the banknote includes a first banknote, and a second banknote that is stored in a stacked state on the first banknote, and
wherein the banknote management method further comprises:
receiving a serial number of the first banknote, and first disinfection information of the first banknote that is information relating to a state of disinfection of the first banknote;
receiving a serial number of the second banknote, and first disinfection information of the second banknote that is information relating to a state of disinfection of the second banknote; and
updating the first disinfection information of the first banknote in accordance with the first disinfection information of the second banknote when the first disinfection information of the second banknote indicates that the first disinfection information of the second banknote is inferior to the first disinfection information of the first banknote in terms of a state of disinfection.

5. The banknote management method according to claim 4, wherein the updating the first disinfection information of the first banknote in accordance with the first disinfection information of the second banknote is replacing the first disinfection information of the first banknote with the first disinfection information of the second banknote.

6. The banknote management method according to claim 1,
wherein the computer is communicatively connected to a first banknote processing apparatus, the first banknote processing apparatus including a first serial number reading apparatus and a first disinfection apparatus;
wherein the serial number is a serial number of the banknote read by the first serial number reading apparatus; and
wherein the first disinfection information is information relating to a state of disinfection of the banknote performed by the first disinfection apparatus.

7. The banknote management method according to claim 6,
wherein the computer is communicatively connected to a second banknote processing apparatus, the second banknote processing apparatus including a second serial number reading apparatus, and
wherein the banknote management method further comprises:

receiving a serial number of the banknote read by the second serial number reading apparatus; and
determining details of a process to be performed on the banknote by the second banknote processing apparatus in accordance with the first disinfection information.

8. The banknote management method according to claim 7, wherein the determining of the details of the process to be performed on the banknote by the second banknote processing apparatus includes determining whether disinfection is to be performed on the banknote by a second disinfection apparatus provided in the second banknote processing apparatus.

9. The banknote management method according to claim 7, further comprising:
receiving second disinfection information that is information relating to a state of disinfection of the banknote performed by a second disinfection apparatus provided in the second banknote processing apparatus; and
updating the first disinfection information recorded in the recording apparatus in accordance with the second disinfection information when, after the serial number is read by the first serial number reading apparatus and the banknote is disinfected by the first disinfection apparatus, the serial number is read by the second serial number reading apparatus, and the banknote is disinfected by the second disinfection apparatus.

10. The banknote management method according to claim 1, wherein the recording apparatus is installed in a container which the banknote is stored when the banknote is transported.

11. The banknote management method according to claim 1, wherein the disinfection is performed through at least one of irradiation of the banknote with an ultraviolet ray, contact between the banknote and a disinfecting material, and heating of the banknote.

12. The banknote management method according to claim 1, further comprising:
determining an index representing ease regarding handling the banknote in accordance with the first disinfection information; and
outputting the index.

13. A banknote management system comprising:
a first banknote processing apparatus including a first serial number reading apparatus configured to read a serial number of a banknote, and a first disinfection apparatus configured to disinfect the banknote;
a recording apparatus; and
processing circuitry configured to receive the serial number of the banknote read by the first serial number reading apparatus and first disinfection information relating to a state of disinfection of the banknote disinfected by the first disinfection apparatus, the banknote whose serial number has been read by the first serial number reading apparatus being disinfected by the first disinfection apparatus,
record the serial number and the first disinfection information in association with each other in the recording apparatus, and
associate the state of disinfection of each banknote processed by the first banknote processing apparatus with the serial number.

14. The banknote management system according to claim 13, further comprising:
a second banknote processing apparatus including a second serial number reading apparatus configured to read the serial number of the banknote, wherein the processing circuitry is configured to determine details of a process to be performed on the banknote by the second banknote processing apparatus in accordance with the first disinfection information.

15. The banknote management system according to claim 14,
wherein the second banknote processing apparatus includes a second disinfection apparatus configured to disinfect the banknote; and
wherein the processing circuitry is configured to update the first disinfection information recorded in the recording apparatus in accordance with second disinfection information that is information relating to a state of disinfection of the banknote disinfected by the second disinfection apparatus when, after the serial number of the banknote is read by the first serial number reading apparatus and the banknote is disinfected by the first disinfection apparatus, the serial number of the banknote is read by the second serial number reading apparatus, and the banknote is disinfected by the second disinfection apparatus.

16. The banknote management system according to claim 14, wherein the first banknote processing apparatus and the second banknote processing apparatus are disposed in a same facility.

17. The banknote management system according to claim 14, wherein the first banknote processing apparatus and the second banknote processing apparatus are disposed in facilities different from each other.

18. The banknote management system according to claim 14, further comprising a container configured to be detachable to the first banknote processing apparatus and the second banknote processing apparatus, and to store the banknote in an externally inaccessible manner.

19. The banknote management system according to claim 13, wherein the processing circuitry is incorporated in the first banknote processing apparatus, the processing circuitry being configured to perform entire control of the first banknote processing apparatus.

20. The banknote management system according to claim 19, wherein the recording apparatus is a recording medium incorporated in the first banknote processing apparatus.

* * * * *